United States Patent [19]

Perrier et al.

[11] Patent Number: 5,453,443
[45] Date of Patent: Sep. 26, 1995

[54] BIS(ARYLOXY)ALKANES AS INHIBITORS OF PHOSPHOLIPASE $A_2$ ENZYMES

[75] Inventors: Helene Perrier, Velle Ile Perrot; Petpiboon Prasit, Kirkland; Ian Street, St.-Lazare; Zhaoyin Wang, Pierrefonds, all of Canada

[73] Assignee: Merck Frosst Canada, Inc., Kirkland, Canada

[21] Appl. No.: 277,854

[22] Filed: Jul. 20, 1994

[51] Int. Cl.⁶ .................................................. A61K 31/19
[52] U.S. Cl. .......................... 514/570; 514/571; 514/533; 514/534; 514/545; 560/11; 560/15; 560/60; 562/429; 562/431; 562/459; 562/463; 562/470; 562/472
[58] Field of Search .................... 562/429, 431, 562/459, 463, 470, 472; 560/11, 15, 60; 514/570, 571, 533, 532, 545

[56] References Cited

U.S. PATENT DOCUMENTS 4,820,867  4/1989  Belanger et al. ........................ 562/478
5,135,940  8/1992  Belanger et al. ........................ 514/381

FOREIGN PATENT DOCUMENTS

0476849A2  3/1992  European Pat. Off. .
0501779A1  9/1992  European Pat. Off. .
0509719A1  10/1992  European Pat. Off. .

*Primary Examiner*—José G. Dees
*Assistant Examiner*—Samuel Barts
*Attorney, Agent, or Firm*—Curtis C. Panzer; David L. Rose

[57] ABSTRACT

Compounds having the formula I:

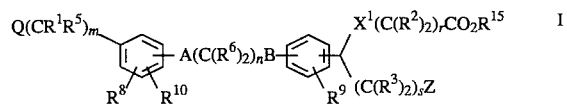

are inhibitors of the $PLA_2$s enzymes. These compounds are useful as anti-allergic, anti-asthmatic, they are also useful in treating various inflammatory diseases such as rheumatoid arthritis, osteoarthritis, bursitis, psoriasis; immunoinflammatory disorders such as contact dermatitis, irritable bowel disease and the like.

12 Claims, No Drawings

BIS(ARYLOXY)ALKANES AS INHIBITORS OF PHOSPHOLIPASE A₂ ENZYMES

BACKGROUND OF THE INVENTION

Eicosanoids are an important class of lipid mediators which modulate a wide variety of physiological functions and play a central role in a number of inflammatory diseases such as asthma, arthritis, and psoriasis. In many cell types the rate-determining step in the generation of eicosanoids is the release of arachidonic acid (AA) from its cellular store in the phospholipid pool. A number of different pathways for the mobilization of AA have been proposed, but many detailed studies of the distribution and stoichiometry of metabolites have demonstrated the importance of phospholipase $A_2$ ($PLA_2$) as a major mediator of agonist-induced AA release [Imai, A., Yano, K., Kameyama, Y., and Nozawa, Y. (1992) *Japan J. Exp. Med.* 52, 99–105; Maede, C. J., Turner, G. A., and Bateman, P. E. (1986) *Biochem. J.* 238, 425–436; Chau, L. -Y. and Tai, H. -H. (1983) *Biochem. Biophys. Res. Commun.* 113, 241–247]. Over the past decade a number of distinct types of $PLA_2$ have been isolated and characterized. The best known of these are; a family of 14-kDa calcium-dependent secreted enzymes, and an 85-kDa cytosolic calcium-dependent enzyme ($cPLA_2$). The 14-kDa enzymes are secreted from the cell into the extracellular environment where they participate in the digestion of biological materials. The $cPLA_2$ is found in low abundance in the cell, and is thought to be involved in the release of AA for eicosanoid production since it preferentially hydrolyzes phospholipids containing AA at the sn-2 position [Clark, J. D., Lin, L. L., Kriz, R. W., Ramesha, C. S., Sultzman, L. A., Lin, A. Y., Milona, N., and Knopf, J. L. (1991) *Cell* 65, 1043–1051; Hanel, A. M., Shcuttel, S., and Gelb, M. H. (1993) *Biochemistry* 32, 5949–59581, responds to physiological changes in calcium concentration by translocating to membranes [Clark, J. D., Lin, L. L., Kriz, R. W., Ramesha, C. S., Sultzman, L. A., Lin, A. Y., Milona, N., and Knopf, J. L. (1991) *Cell* 65, 1043–1051; Kramer, R. M., Roberts, E. F., Manetta, J. V., Sportsman, J. R., and Jakubowski, J. A. (1993) *J. Lip. Mediators* 6, 209–216], and is activated by hormonal signaling through phosphorylation of a serine residue [Lin, L. L., Wartmann, M., Lin, A. Y., Knopf, J. L., Seth, A., and Davis, R. J. (1993) *Cell* 72, 269–278; Lin. L. L., Lin, A. Y., and Knopf, J. L. (1992) *Proc. Natl. Acad. Sci. U.S.A.* 89, 6147–6151].

Since it is proposed that the $cPLA_2$ plays a major role in the mobilization of AA for eicosanoid biosynthesis selective inhibitors of this enzyme may be of use in controlling a wide variety of inflammatory diseases.

SUMMARY OF THE INVENTION

The present invention is directed to electrophilic ketones of Formula I

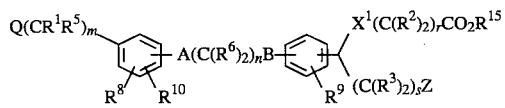

having activity as $PLA_2$ inhibitors. The invention is also directed to methods for the preparation of compounds of Formula I, and to methods and pharmaceutical formulations for using these compounds in a patient in need thereof.

As $PLA_2$ inhibitors the compounds of Formula I are useful as anti-asthmatic, anti-allergic, anti-inflammatory, and cytoprotective agents.

DETAILED DESCRIPTION OF THE INVENTION

Im one embodiment the invention is directed to compound of Formula I

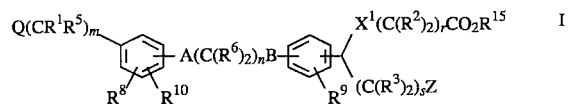

wherein:

$R^1$ is selected from
  (a) hydrogen,
  (b) —$C_{1-6}$alkyl, and
  (c) —$C_{1-6}$alkyl-phenyl;
or wherein $R^1$ and $R^5$ are joined such that together with the carbon atoms to which they are attached there is formed a saturated or unsaturated carbon ring of 3, 4, 5, 6, 7 or 8 atoms;

$R^2$ and $R^3$ are each independently selected from
  (a) hydrogen,
  (b) —$C_{1-6}$alkyl,
  (c) —$C_{1-6}$alkyl-phenyl,
or wherein two $R^2$ or two $R^3$ are joined such that together with the carbon atoms to which they are attached there is formed a saturated or unsaturated carbon ring of 3, 4, 5, 6, 7 or 8 atoms;

$R^5$ is as defined above or is selected from
  (a) hydrogen,
  (b) —$C_{1-6}$alkyl,
  (c) —$C_{1-6}$alkyl-phenyl$C_{1-6}$alkyl,
  (d) —OH,
  (e) —O—$C_{1-6}$alkyl, or
  (f) —O—$C_{1-6}$alkyl-phenylC 1-6alkyl;

$R^6$ is selected from
  (a) hydrogen,
  (b) —$C_{1-6}$alkyl,
  (c) —$C_{1-6}$alkyl-phenyl, wherein the phenyl is optionally substituted with $C_{1-2}$alkyl;
  (d) —OH,
  (e) —O—$C_{1-6}$alkyl, or
  (f) —O—$C_{1-6}$alkyl-phenyl, wherein the phenyl is optionally substituted with $C_{1-2}$alkyl;
or wherein two $R^6$ are joined to form O═ or are joined together such that together with the carbon atom to which they are attached there is formed a saturated or unsaturated carbon ring of 3, 4, 5, 6, 7 or 8 atoms;

$R^8$, $R^9$ and $R^{14}$ are each independently selected from
  (a) H,
  (b) —$C_{1-6}$alkyl,
  (c) halo,
  (d) —CN,
  (e) —OH,
  (f) —$OC_{1-6}$alkyl,
  (g) —$OC_{1-6}$alkyl-phenyl,
  (h) —$SR^{11}$,
  (i) $S(O)R^{11}$, or
  (j) $S(O)_2R^{11}$;

$R^{10}$, $R^{15}$, $R^{16}$ and $R^{17}$ are each independently selected from
  (a) hydrogen, (b) —$C_{1-6}$alkyl, and (c) —$C_{1-6}$alkyl-phenyl;

$R^{11}$ is selected from (a) —$C_{1-6}$alkyl, (b) —$C_{2-6}$alkenyl, (c) —$CF_3$, (d) —phenyl$(R^{12})_2$, or (e) —$C_{2-6}$alkenyl-phenyl$(R^{12})_2$, $R^{12}$ is (a) hydrogen, (b) —$C_{1-6}$alkyl, (c) Cl, F, I or Br;

$R^{13}$ is perfluoro$C_{1-6}$alkyl;

A and B are each independently (a) covalent bond, (b) O, (c) S, (d) S(O), or (e) $S(O)_2$;

Q is selected from (a) —CH(OH)$R^{13}$, (b) —COR$^{13}$, (c) —COR$^{16}$, or (d) —$C_{1-4}$alkylCOCOOR$^{17}$;

$X^1$ is selected from (a) —O—, (b) —S—, (c) —S(O)—, (d) —$S(O)_2$—;

Z is (a) H, or (b) —phenyl—$(R^{14})_3$, m is 0, 1, 2, 3 or 4 n is 2, 3, 4, 5, 6 or 7;

r and s are each independently 0, 1, 2, 3, 4, 5, 6, 7 or 8.

Preferred compounds of Formula I are those of Formula Ia:

$$Q(CR^1R^5)_m\text{-Ar}(R^8)(R^{10})\text{-A-CH}_2\text{-CH}(R^6)\text{-CH}_2\text{-O-Ar-CH}(X^1(C(R^2)_2)_rCO_2R^{15})((C(R^3)_2)_sZ)$$ Ia wherein:

$R^8$ is H, OH or OMe;

$R^{10}$ is H, n-Pr or halogen;

A is O or S;

$X^1$ is O or S; and the remaining substituents are as defined above.

The terms alkyl, alkenyl, and alkynyl mean linear, branched and cyclic structures and combinations thereof.

The term "alkyl" includes "cycloalkyl" and extends to cover carbon fragments including methyl, ethyl, propyl, isopropyl, butyl, s- and t-butyl, pentyl, hexyl, heptyl, and the like. Specific abbreviations used in this specification include:

Me=methyl

Et=ethyl n-Pr=normal propyl i-Pr=isopropyl n-Bu=normal butyl s-Bu=isobutyl t-Bu=secondary butyl c-Pr=cyclopropyl c-Bu=cyclobutyl c-Pen=cyclopentyl c-Hex=cyclohexyl "Perfluoro$C_{1-6}$alkyl" is an alkyl group in which all the hydrogen atoms have been replaced by fluorine atoms.

"Alkylphenyl" means a phenyl group attached to the end of a alkyl group.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt, thereof, and may also contain a pharmaceutically acceptable carder and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,$N^1$-dibenzylethylenediamine, diethylamine, 2-diethylamino-ethanol, 2-dimenthylaminoethanol, ethanolamine, ethylenediamine, N-ethylmorpholine, N-ethylpiperidine, glucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutical acceptable salts.

The ability of the compounds of Formula 1 inhibit actions of the $PLA_2$s makes them useful for preventing or reversing the symptoms induced by the arachidonic acid in a human subject. This inhibition of the $PLA_2$s indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation and the like, 7) renal insufficiency arising from ischemia induced by immunological or chemical (cyclosporin) etiology, 8) migraine or cluster headache, 9) ocular conditions such as uveitis, 10) hepatitis resulting from chemical, immunological or infectious stimuli, 11 ) trauma or shock states such as burn injuries, endotoxemia and the like, 12) allograft rejection, 13) prevention of side effects associated with therapeutic administration of cytokines such as Intefieukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The magnitude of prophylactic or therapeutic dose of a compound of Formula I will of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably form about 1 mg to about 10 mg) of a compound of Formula 1 per kg of body weight per day.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the an of pharmacy.

For administration by inhalation, the compounds of the present invention are conveniently delivered in the form of an aerosol spray presentation form pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of Formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carder may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the lime in the case of oral solid preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carder which constitutes one or more necessary ingredients. In general, the compositions are prepared by uniformly and intimately admixing the active ingredient with liquid carders or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Providone | 14.0 |
| Pregelantinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

Methods of Synthesis

Compounds of the present invention can be prepared according to the following methods. Temperatures are in degrees Celsius.

Method A

An aldehyde such as hydroxybenzaldehyde II or protected with a group such as tert-butyl diphenylsilyl is treated with a Grignard reagent in a solvent such as ether to give alcohol III. Compound III can be protected with a reagent such as dihydropyran in a solvent such as dichloromethane with a catalyst such as PPTS to give IV. Deprotection of the protected phenol, with a reagent such as tetrabutylammonium fluoride affords V. Coupling of III or V with a reagent such as dibromopropane and a base such as potassium carbonate in a solvent such as acetone gives the alcohol VIa or VIb. Reaction of VIa or VIb with a substituted phenol in the same coupling reaction as above gives VIIa or VIIb which treatment with a Lewis Acid such as $BF_3 \cdot OEt_2$, $ZnI_2$, $ZnCl$, etc. and an appropriate thiol or alcohol give the Compound IA. Compound IA wherein $R^{15} \neq H$ can be hydrolyzed with a base such as LiOH to give IA (wherein $R^{15}=H$).

METHOD A

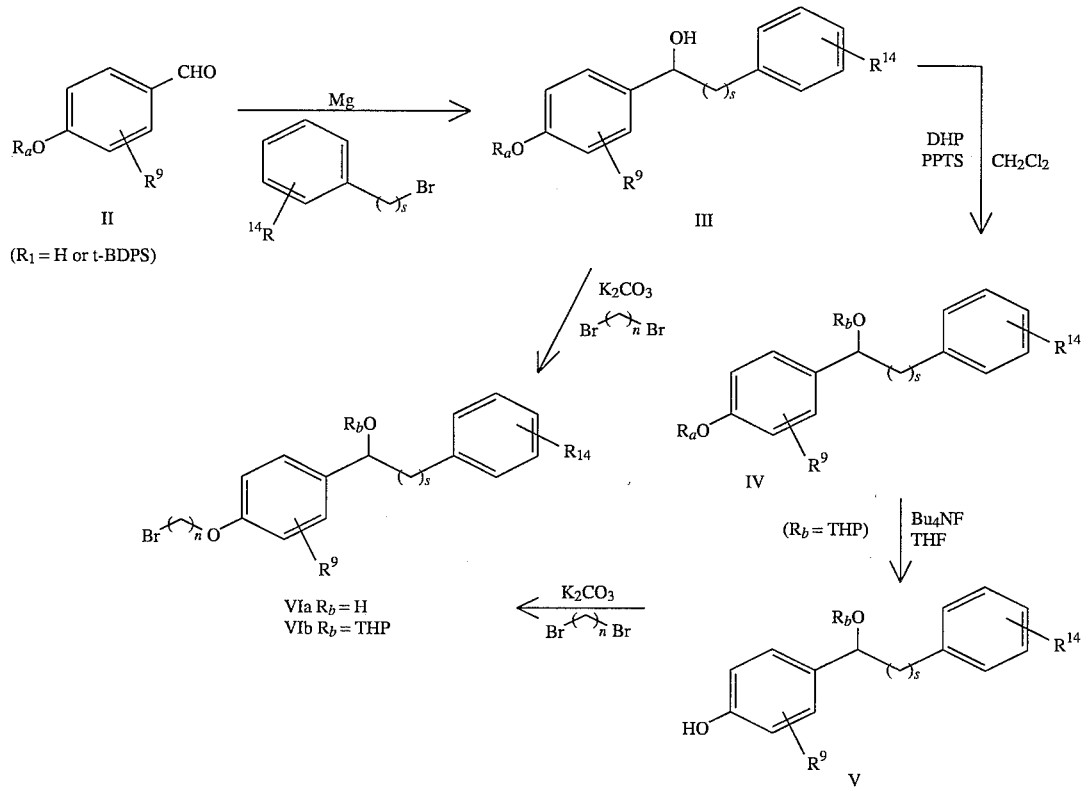

-continued
METHOD A

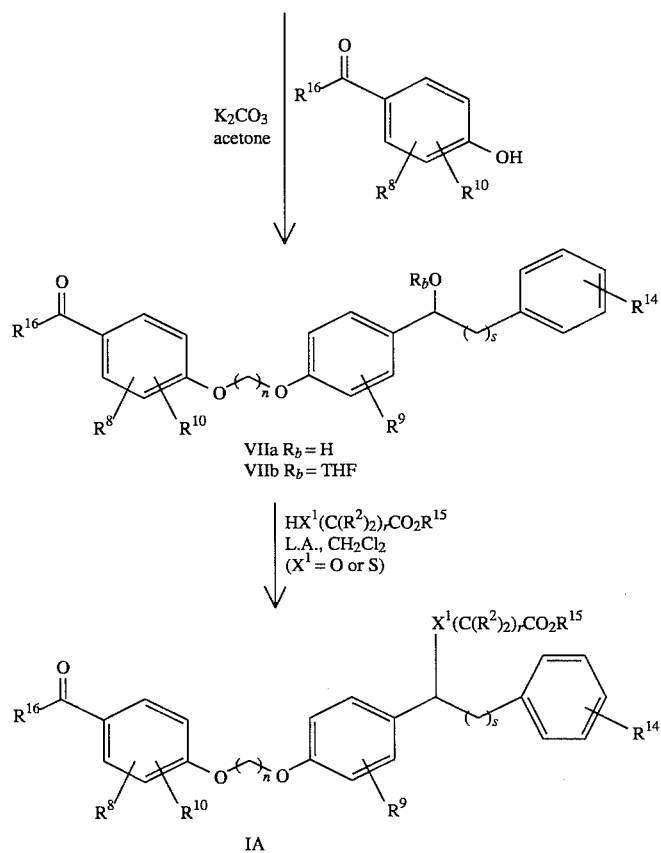

Method B

The Compound VIa or VIb, obtained from Method A, can be coupled with an appropriate bromophenol or bromothiophenol, as described in Method A, to give Compound VIIIa or VIIIb. Compound VIIIa and VIIIb is treated with a strong base such as noBuLi and treatment with an electrophile such as ethyl trifluoroacetate, ethyl pentafluoropropionate or dimethyl oxalate gave respectively IXa or IXb and Xa or Xb. These compounds are converted to the final Compound IB or ID using the procedure described in Method A. Compound IB is reduced with a reagent such as sodium borohydride to give the corresponding alcohol IC.

METHOD B

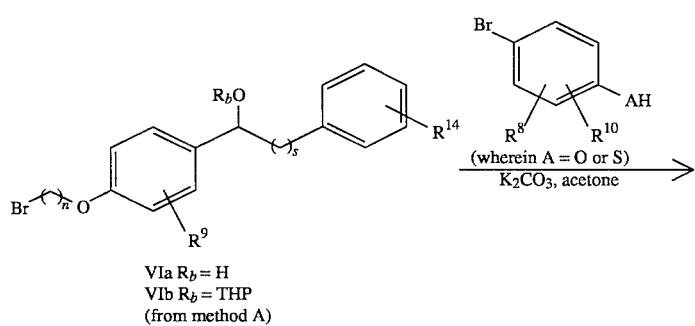

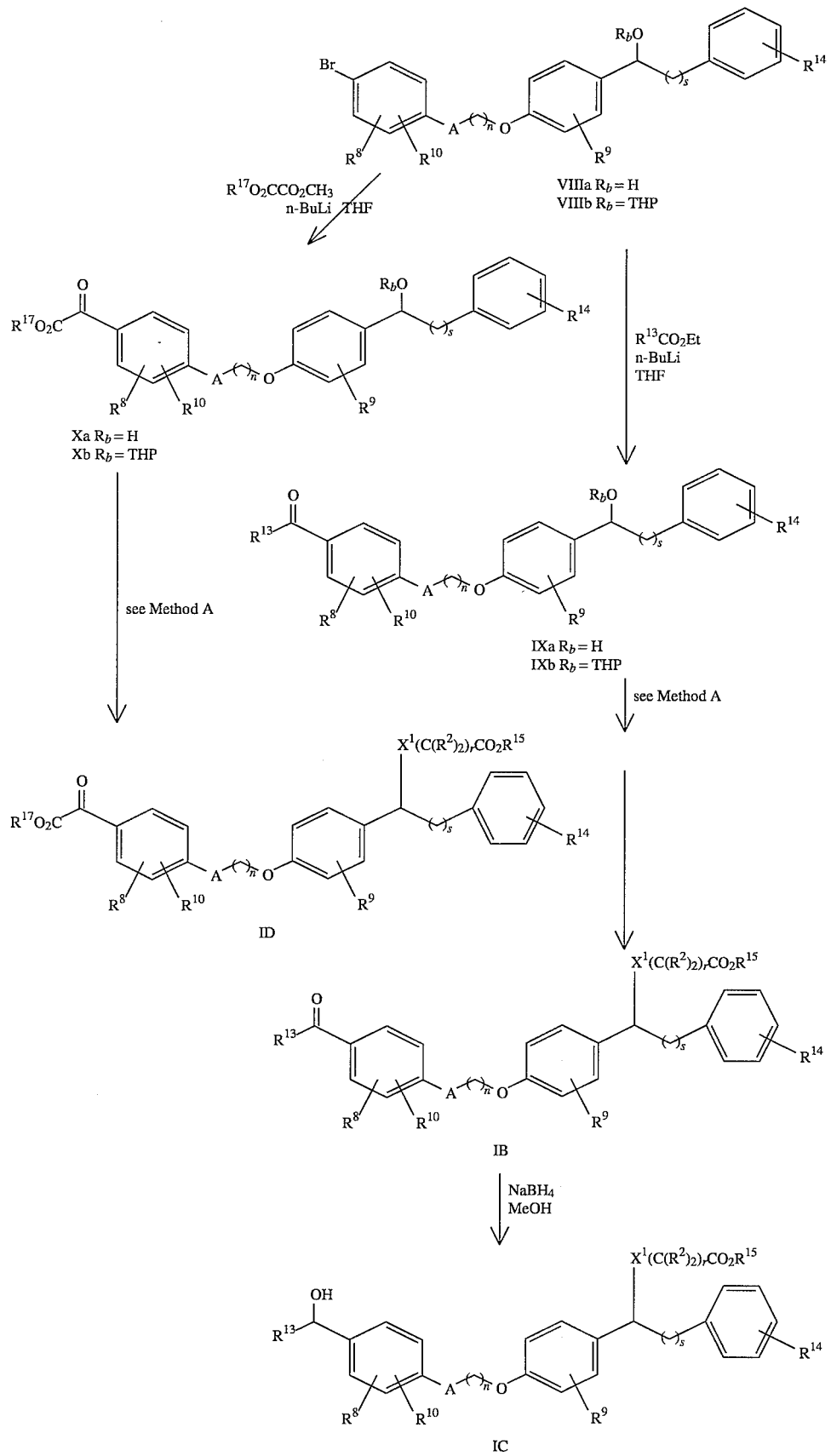

Method C

VIa or VIb, obtained from Method A is coupled with an appropriate phenol such as described in Method A to give Compound XIa or XIb. Hydrolysis of XIa or XIb with a base such as lithium hydroxide gives XIIa or XIIb. This compound is converted to the desired thioether XIII by Method A. Compound XIII is treated with a reagent such as oxalyl chloride to give the acid chloride which is treated with an acid such trifluoroacetic acid anhydride and a base such as pyridine to give the trifluoromethylketone IE. Compound IE (wherein $R^{15} \neq H$) can be hydrolysed by a base such as lithium hydroxide to give IE (wherein $R^{15}=H$).

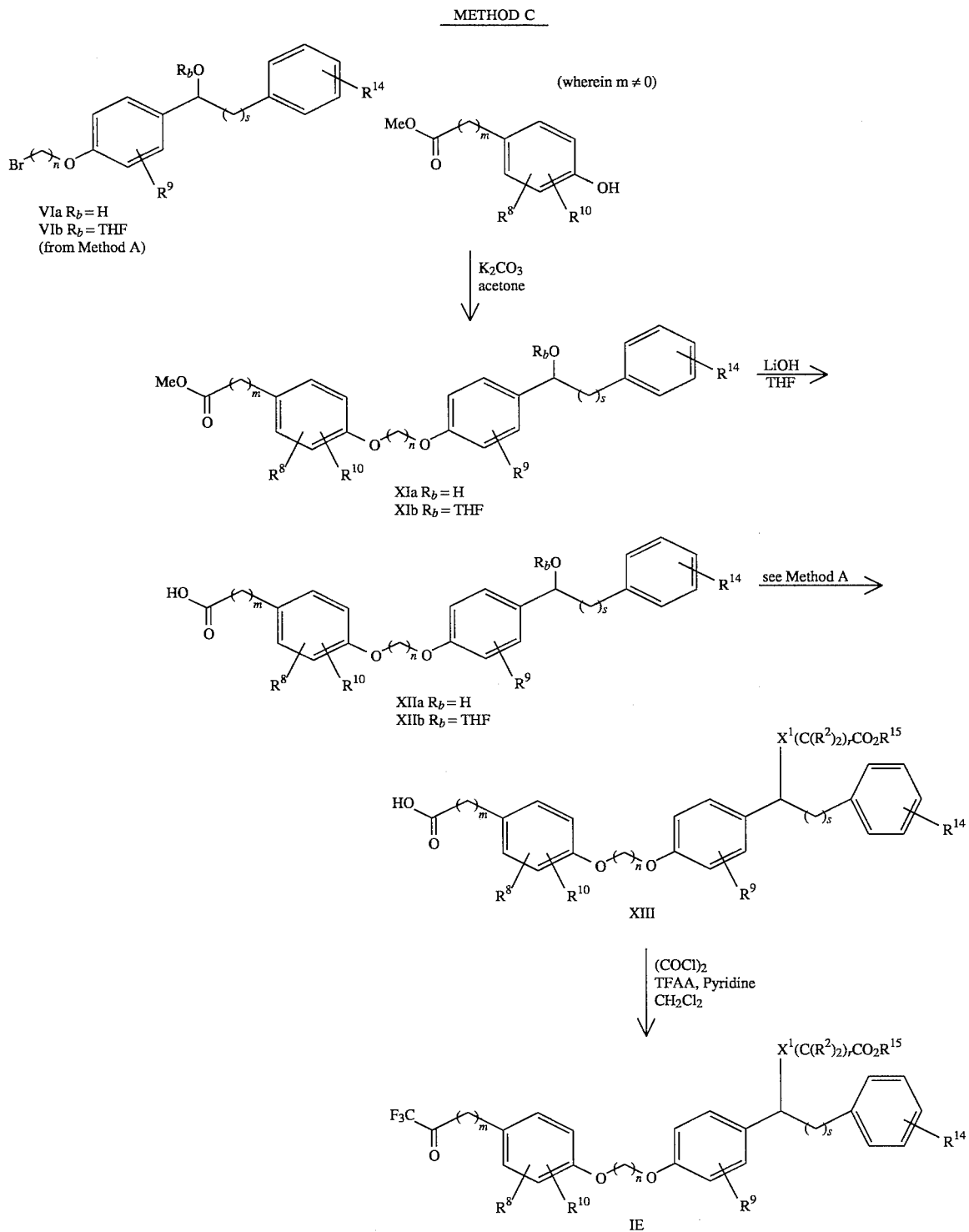

Method D

Compound III, from Method A, is reacted with an alkylating agent such as epichlorohydrin in solvent like ethanol with a base such as KOH to give Compound XIV. This compound is protected by treatment with a reagent such as DHP and PPTS in a solvent like ethanol to give Compound XV. Compound XV is alkylated with a suitable phenol XVI and a base such as Triton B in a solvent such as DMF to give XVII. Alkylation of XVII with a reagent $R^7Br$ in a solvent such as DMF with a base such as NaH affords XVIII. This compound is converted to IF as described in Method A.

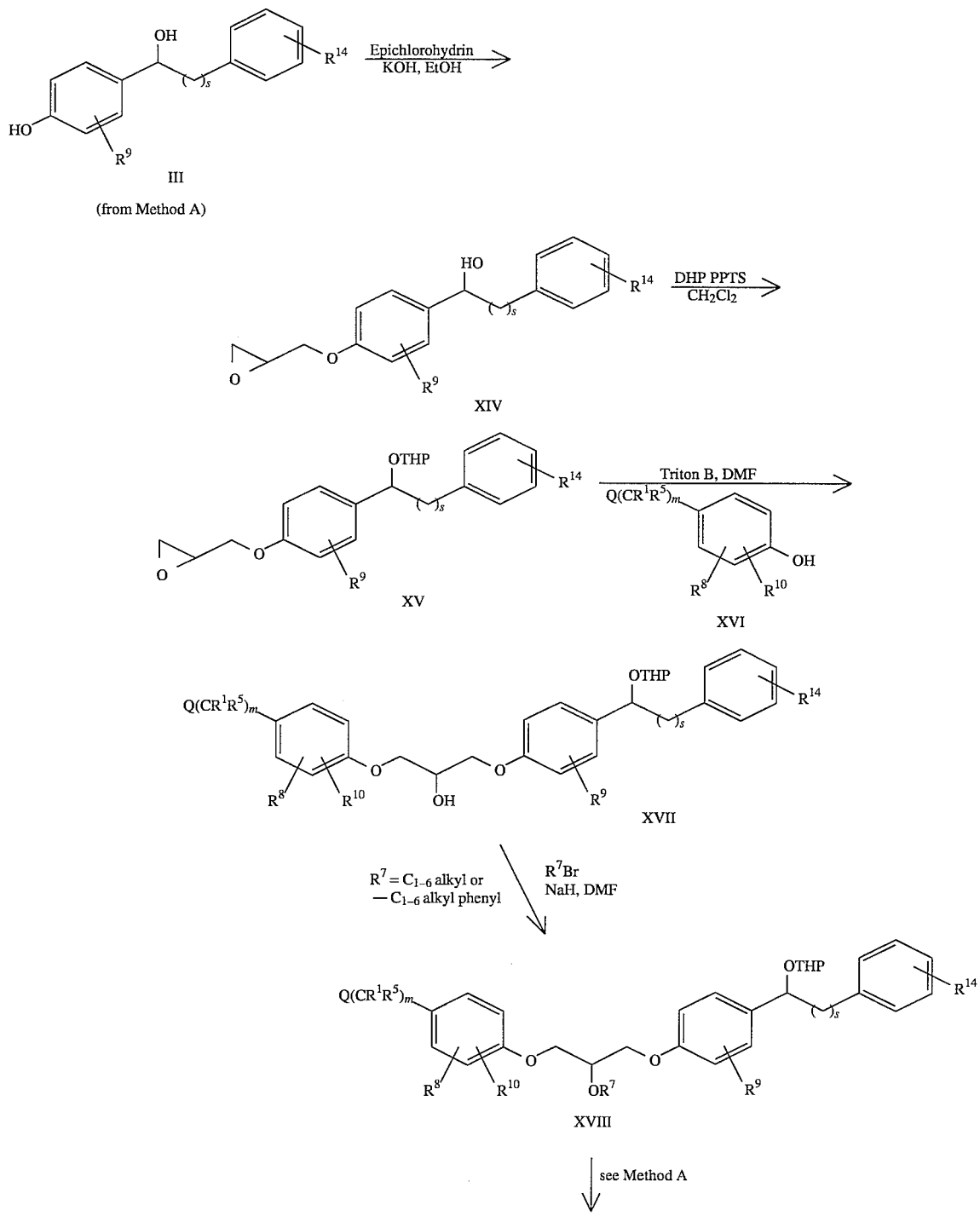

-continued
METHOD D

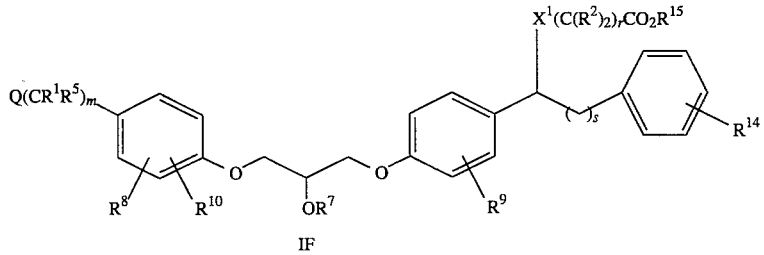

IF

Method E

Compounds VIIa (from Method A) IXa and Xa (from Method B), XIa and XIIa (from Method C) are converted to IG with an alkylating agent such as XIX with a base like sodium hydride in a solvent like DMF to give the corresponding ether IG ($R^{15} \neq H$). Compound IG (wherein $R^{15} \neq H$) could be hydrolysed with a base such as lithium hydroxide to give IG (wherein $R^{15}=H$).

METHOD E

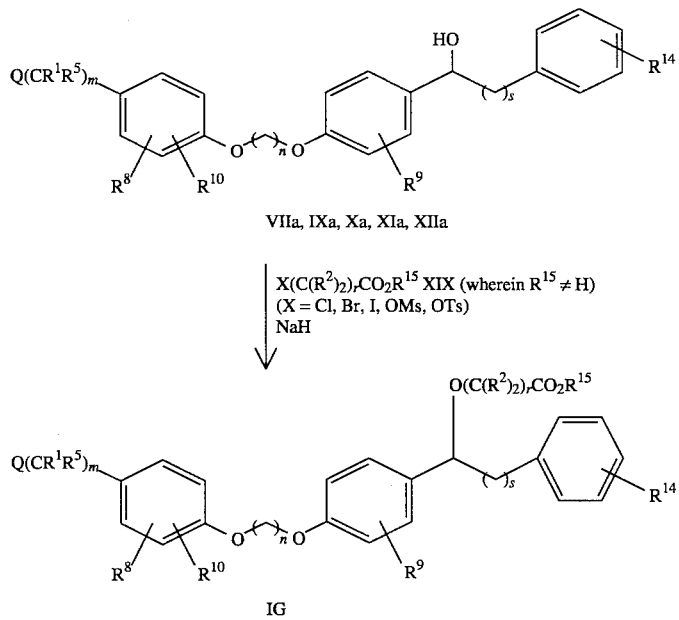

VIIa, IXa, Xa, XIa, XIIa

IG

REPRESENTATIVE COMPOUNDS

Table 1 illustrates compounds of which are representative of the present invention.

ASSAYS FOR DETERMINING BIOLOGICAL ACTIVITY

The $PLA_2$ inhibitory properties of the compounds of the present invention are evaluated using the following assays.
Inhibition of release of unesterified arachidonic acid in U937 cells Human U937 cells were obtained from the American Type Cultures Collection and cultured in RPMI 1640 medium supplemented with 10% fetal bovine serum, penicillin and streptomycin. Four days before the measurement the cells were seeded at about $0.12 \times 10^6$ cells/ml into the same medium containing 1.3% dimethylsulfoxide. The culture was centrifuged and resuspended in Hank's Balanced Salt solution containing 1.4 mM $CaCl_2$, 0.7 mM $MgSO_4$ and 15 mM Hepes at about $2 \times 10^6$ cells/ml.

0.25 ml cells were incubated for 2 or 3 minutes at 37° C. with 0.001 ml dimethyl sulfoxide as vehicle control or 0.001 ml dimethyl-sulfoxide containing the test compound. A 5 mM solution of compound A23187 in dimethylsulfoxide was diluted 20 fold with Hank's Balanced salt solution, and 0.01 ml was added to the cells. Measurement of the resting level of Arachidonic acid was made on cells that received 0.01 ml of 5% dimethylsulfoxide diluted in Hank's solution. After 3 minutes incubation of the cells 1.25 ml Dole's solvent mixture (1.20 ml isopropanol, 30 ml heptane, 3 ml 1 N sulfuric acid) was added.

50 ng $D_8$-Arachidonic acid was added to each tube of cells and to tubes containing 0.2–200 ng Arachidonic acid standards in the same mixture as the cells, but without cells. 0.5 ml water and 0.75 ml heptane was added to each tube, each was vortexed, and the phases allowed to separate. 0.5 or 0.75 ml of the heptane phase was removed, dried under vacuum, allowed to react with 0.1 ml of a mixture of 10 ml acetonitrile, 1 ml diisopropylethylamine and 0.01 ml pentafluorobenzylbromide at 60° C. for 15 minutes. The sample was dried under vacuum, redissolved in 1 ml dodecane and analysed for its content of Arachidonic acid and $D_8$-Arachidonic acid by gas chromatography-mass spectrometry by resonance electron capture ionization, monitoring the ions at m/z 303 and 311. The content of Arachidonic acid in test samples was calculated from the ratio of signal obtained at m/z 303 to the signal obtained at m/z 311 compared with the same ratio calculated for Arachidonic acid standards.

The rise in Arachidonic acid that was stimulated by A23187 was calculated as the difference between the values in the presence and absence of A23187, both in the absence of test compound (Ratio 1 ). Similarly, Ratio 2 was calculated for the difference in values between Arachidonic acid in the absence of A23187 and Arachidonic acid in the presence of both A23187 and the test compound. Inhibition of unesterified Arachidonic acid release was calculated as: 100−((Ratio 2/Ratio 1 )×100). In this assay, Examples 1–20 inhibited unesterified arachidonic acid release at a concentration range of 0.5 to 10 μM.

EXAMPLES

The invention will now be illustrated by the following non-limiting examples in which, unless stated otherwise:

All operations were carried out at room or ambient temperature, that is, at a temperature in the range 18°–25° C.; evaporation of solvent was carded out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), tool (moles), mmol (millimoles), eq (equivalent(s)).

The following abbreviations have the indicated meanings:

Ac=acetyl
Bn=benzyl
DBU=1,8-diazabicyclo[5.4.0]undec-7-ene
DIBAL=diisobutylaluminum hydride
DMAP=4-(dimethylamino)pyridine
DMF=N,N-dimethylformamide
Et$_3$N=triethylamine
LDA=lithium diisopropylamide
m-CPBA=metachloroperbenzoic acid
MMPP=monoperoxyphtalic acid
MPPM=monoperoxyphthalic acid, magnesium salt 6H$_2$O
Ms=methanesulfonyl=mesyl=SO$_2$Me
MsO=methanesulfonate=mesylate
NSAID=non-steroidal anti-inflammatory drug
OXONE®=2KHSO$_5$·KHSO$_4$·K$_2$SO$_4$
PCC=pyridinium chlorochromate
PDC=pyridinium dichromate
Ph=phenyl
Phe=benzenediyl
Pye=pyridinediyl
r.t.=room temperature
rac.=racemic
SAM=aminosulfonyl or sulfonamide or SO$_2$NH$_2$
TBAF=tetra-n-butylammonium fluoride
Th=2- or 3-thienyl
TFAA=trifluoroacetic acid anhydride
THF=tetrahydrofuran
Thi=thiophenediyl
TLC=thin layer chromatography
TMS-CN=trimethylsilyl cyanide
Tz=1H (or 2H)-tetrazol-5-yl
C$_3$H$_5$=allyl

EXAMPLE 1

3-(1-{4-[3-(4-Acetyl-3-hydroxy-2-propylphenoxy)propoxy]phenyl }- 4-phenylbutylthio)propionic acid sodium salt Step 1: 4-(1-Hydroxy-4-phenylbutyl)phenol To a 0° C. solution of 4-hydroxybenzaldehyde (6.1 g) in THF (75 mL) is added a 3.6 M ethereal solution of 3-phenylpropyl-magnesium bromide (30.5 mL). The resulting suspension was stirred at 25° C. for 16 hrs. and then transferred slowly into ice cold 25% aqueous NH$_4$OAc. The product was extracted into EtOAc (3×100 mL) and the combined extracts were washed with brine, dried with MgSO$_4$ and the solvents were removed under reduced pressure. The residue was swished in a 1:5 mixture of EtOAc and hexanes for 2 hrs. and the solid was filtered and dried to yield the title compound.

$^1$H NMR (CD$_3$COCD$_3$) δ1.5–1.8 (4H, m), 2.55–2.65 (2H, t), 4.0 (1H, s), 4.55–4.65 (1H, t), 6.7–6.8 (2H, d), 7.10–7.30 (7H, m), 8.2 (1H, br-s).

Step 2: 1-(2-Hydroxy-4-{3-[4-(1-hydroxy-4-phenylbutyl)phenoxy] propoxy},3-propylphenyl)ethanone To a solution of 3-(4-acetyl-3-hydroxy-2-propylphenoxy)propyl bromide (J. Med. Chem. 29, 1573–1576, 1986) (315 mg) and the phenol of Step 1 (242 mg) in acetonitrile (5 mL) was added cesium carbonate (650 mg) and the mixture was heated to reflux for 5 hrs. The suspension was cooled to 25° C. and poured into 25% aqueous NH$_4$OAc and EtOAc. The organic layer was washed with brine, dried with MgSO$_4$ and the solvents are removed in vacuo. The residue was purified by chromatography on silica gel using EtOAc and hexanes (1:2) to yield the title compound.

$^1$H NMR (CD$_3$COCD$_3$) δ0.8–1.0 (3H, t), 1.40–1.80 (6H, m), 2.25– 2.35 (2H, q), 2.50–2.75 (7H, m), 4.0–4.1 (1H, s), 4.15–4.25 (2H, t), 4.25–4.35 (2H, t), 4.55–4.65 (1H, t), 6.65–6.75 (1H, d), 6.85–6.95 (2H, d), 7.10–7.30 (7H, m), 7.70–7.80 (1H, d).

Step 3: 3-(1-{4-[3-(4-Acetyl-3-hydroxy-2-propylphenoxy)propoxy] phenyl}-4-phenylbutylthio)propionic acid sodium salt To a 0° C. solution of the alcohol from Step 2 (275 mg) and 3-mercaptopropionic acid (64 mg) in 1,2-dichloroethane (10 mL) was added $BF_3 \cdot OEt_2$ (355 mg). After 1 hr. at 0° C., the reaction mixture was poured on 25% aqueous $NH_4OAc$ containing AcOH (3 drops) and EtOAc. The organic layer was separated and the aqueous further extracted with EtOAc (2×10 mL). The combined organic layers were washed with brine, dried with $MgSO_4$ and solvents were removed under reduced pressure to yield an oil which was spectroscopically pure. The oil was dissolved in EtOH and 2N NaOH (1 equivalent) was added. Ethanol was removed under reduced pressure and the residue was dissolved in $H_2O$ and freeze dried to yield the title compound as a hemihydrate.

Analysis calculated for $C_{32}H_{37}O_6SNa \cdot \frac{1}{2} H_2O$: C, 66.07; H, 6.41; S, 5.51; Na, 3.95

Found: C, 66.33; H, 6.46; S, 5.30; Na, 4.00

EXAMPLE 2

3-[ 1-{4-[3-(4-Acetyl-3-hydroxy-2-propylphenoxy)propoxy]phenyl}-4-( 4-hydroxyphenyl)butylthio]propionic acid methyl ester Step 1: 4-{1-(Tetrahydropyran-2-yloxy)-4-[4-tetrahydropyran- 2-yloxy)phenyl]butyl}phenol Following the procedure of Step 1 of Example 1, the title compound was prepared from 4-[3-bromopropyl]phenol and 4-(diphenyl t-butyl silyloxy)benzaldehyde with the presence of 1.0 eq of ethyl magnesium bromide. Protection of the compound as a THP, followed by deprotection with tetrabutylammoniumfluoride in THF, afforded the title compound.

$^1$H NMR (CDCl$_3$) δ1.35–1.62 (12H, m), 1.8–1.9 (4H, m), 2.4–2.47 (1H, t), 2.48–2.6 (2H, m), 3.22–3.32 (1H, m), 3.41–3.51 (1H, m), 3.52–3.62 (2H, m), 3.9–4.0 (2H, m), 4.4 (1H, t), 4.45 (1H, t), 4.6 (1H, t), 4.75 (1H, t), 5.35 (2H, t), 6.7–6.75 (2H, m), 6.8–6.9 (2H, m), 6.95–7.05 (2H, m), 7.1 (2H, d), 7.15 (2H, d).

Step 2: 3-[ 1-{4-[3-(4-Acetyl-3-hydroxy-2-propylphenoxy)propoxy] phenyl}-4-(4-hydroxyphenyl)butylthio]propionic acid methyl ester Following the procedure described in Step 2 and 3 of Example 1, but substituting in Step 2, 4-(1-hydroxy-4-phenylbutyl) phenol for the phenol of Step 1 and substituting in Step 3, 3-mercapto propionic acid for methyl 3-mercaptopropionate, and $BF_3.OEt_2$ for $ZnI_2$, the title compound was prepared.

$^1$H NMR (CDCl$_3$ ): δ0.9 (3H, t), 1.41–1.62 (5H, m), 1.7–1.91 (2H, m), 2.3 (2H, t), 2.4–2.51 (5H, m), 2.54 (3H, s), 2.62 (2H, t), 3.65 (3H, s), 3.73 (1H, t), 4.2 (4H, dt), 4.78 (1H, br-s), 6.48 (1H, d), 6.7 (2H, d), 6.82 (2H, d), 6.95 (12H, d), 7.15 (2H, d), 7.6 (1H, d), 12.7 (1H, s).

EXAMPLE 3

1-(1-{4-[3-(4-Acetyl-3-hydroxy-2-propylphenoxy)propoxy]phenyl}- 4-phenylbutylthiomethyl)cyclopropylacetic acid Step 1: 1-(1-{4-[3-(4-Acetyl-3-hydroxy-2-propylphenoxy) propoxy)phenyl}-4-phenylbutylthiomethyl)cyclopropylacetic acid methyl ester Following the procedure of Step 3 of Example 1, but substituting 3-mercaptopropionic acid for methyl 1-mercaptomethyl cyclopropylacetate (U.S. Pat. No. 5,270,324), and $BF_3.OEt_2$ for $ZnI_2$ afforded the title compound.

$^1$H NMR (CDCl$_3$ ) δ0.3–0.5 (4H, m), 0.9 (3H, t), 1.45–1.65 (4H, m), 1.7–1.9 (2H, m), 2.25–2.4 (6H, m), 2.55 (5H, br-s), 2.65 (2H, t), 3.6 (3H, s), 3.7–3.8 (1H, m), 4.15 (2H, t), 4.25 (2H, t), 6.48 (1H, d), 6.82 (2H, d), 7.1 (2H, t), 7.15–7.3 (5H, m), 7.6 (1H, d), 12.1 (1H, s).

Step2: 1-(1-{4-[3-(4-Acetyl-3-hydroxy-2-propylphenoxy) propoxy)phenyl}-4-phenylbutylthiomethyl)cyclopropylacetic acid Following the procedure of Step 6 of Example 7, the methyl ester of Step 1 was converted to the title compound.

$^1$H NMR (CDCl$_3$ ) δ0.3–0.5 (4H, m), 0.9 (3H, t), 1.5–1.6 (4H, m), 1.7–1.9 (2H, m), 4.15 (2H, t), 4.25 (2H, t), 6.45 (1H, d), 6.82 (2H, d), 7.05–7.3 (7H, m), 7.6 (1H, d), 12.2 (1H, s).

EXAMPLE 4

3-(1-{4-[3-(4-Acetyl-3-hydroxy-2-propylphenoxy)propoxy]phenyl}- 3-phenylpropylthio)propionic acid Following the procedure of Step 1–3 of Example 1, but substituting 3-phenylpropylmagnesium bromide for 3-phenethyl magnesium bromide, the title compound was prepared.

$^1$H NMR (CDCl$_3$ ) δ0.92 (3H, t), 1.52 (2H, m), 2.15 (2H, m), 2.30 (2H, m), 2.55 (3H, s), 2.40–2.68 (8H, m), 3.73 (1H, dd), 4.18 (2H, t), 4.23 (2H, t), 6.47 (1H, d), 6.87 (2H, d), 7.10–7.28 (7H, m), 7.58 (1H, d).

EXAMPLE 5

3-[1-{4-[3-(4-Acetyl-3-hydroxy-2-propylphenoxy)propoxy]phenyl}- 4-(4-hydroxy-3-iodophenyl)butylthiolpropionic acid methyl ester A mixture of the product of Example 2 (100 mg) in ammonium hydroxyde (5 mL) was treated with potassium triiodide. After 15 min., the reaction mixture was poured into pH 7 buffer (10 mL), extracted with EtOAc and washed with sodium thiosulfate (2 mL). The solvent was evaporated and the title compound was purified by flash chromatography on silica with EtOAc and hexanes (1:5).

$^1$H NMR (CDCl$_3$ ) δ0.9 (3H, t), 1.42–1.58 (4H, m), 1.7–1.9 (2H, m), 2.25–2.35 (2H, m), 2.4–2.55 (6H, m), 2.6 (3H, s), 2.63 (2H, t), 3.72 (1H, t), 4.1–4.3 (4H, m), 6.45 (1H, d), 6.7 (1H, d), 6.85 (2H, d), 6.95 (2H, d), 7.2 (2H, d), 7.6 (1H, d), 12.7 (1H, s).

EXAMPLE 6

3-(1-{4-[3-(4-Acetyl-3-hydroxyphenoxy)propoxy]phenyl}-4-phenylbutylthio)propionic acid sodium salt Following the procedure of Step 2 and 3 of Example 1, but substituting 3-(4-acetyl-3-hydroxy-2-propylphenoxy)propyl bromide for 3-(4-acetyl-3-hydroxyphenoxy)propyl bromide (J. Med. Chem. 29, 1573–1576, 1986), the title compound was prepared.

Analysis calculated for $C_{30}H_{33}O_6SNa \cdot 0.5\ H_2O$: C, 65.16; H, 5.98; S, 5.89; Na, 4.22

Found: C, 65.75; H, 5.98; S, 5.70; Na, 4.33

EXAMPLE 7

3-(4-Phenyl-1-{4-[3-(4-trifluoroacetylphenoxy)propoxy] phenyl} butylthio)propionic acid Step 1: 3-(4-Bromophenoxy)propan-1-ol A mixture of 12.5 g of 4-bromophenol, 12 g of $K_2CO_3$ and 16 g of 3-bromo-1-(tetrahydropyran-2-yloxy)propane in 120 mL of acetone was refluxed for 2 days. Et$_2$O (200 mL) and sat. aqueous NH$_4$Cl solution (100 mL) were then added. The ether layer was washed with 50 ml of 5N NaOH, dried over Na$_2$SO$_4$ and concentrated to give 23 g of crude product. The crude product was dissolved in 200 mL of MeOH, and treated with 200 mg of pTSA for 2 hrs. The mixture was then quenched with 0.5 ml of Et$_3$N and concentrated to give the crude title compound.

Step 2: 3-(4-Bromophenoxy)propyl bromide

A solution of 12 g of the crude product from Step 1 and 15 mL of Et$_3$N in 150 mL of CH$_2$Cl$_2$ was cooled to 0° C. Methanesulfonyl chloride (4.65 mL) was added dropwise. After 30 min. at 0° C., the reaction was quenched with sat. NAHCO$_3$ (50 mL), extracted with EtOAc (150 mL), the extract was dried over Na$_2$SO$_4$ and concentrated. The crude product was then dissolved in 150 mL of acetone and treated with 17 g of lithium bromide. The mixture was refluxed for 30 min., and solvent was evaporated. Sat. NaCl (100 mL) and 1:1 Hexane/EtOAc (200 mL) were added and the organic layer was separated, dried over MgSO$_4$ and concentrated to give 15 g of the crude title compound.

Step 3: 1-{4-[3-(4-Bromophenoxy)propoxy]phenyl}-4-phenylbutan- 1-ol

Following the procedure of Step 2 of Example 1, but substituting 3-(4-acetyl-3-hydroxy-2-propylphenoxy)propyl bromide for the bromide from Step 2, the title compound was prepared.

Step 4: 2,2,2-Trifluoro-1-(4-{3-[4-(1-hydroxy-4-phenylbutyl) phenoxy]propoxy}phenyl)ethanone To a solution of the product from Step 3 (0.75 g) in THF (20 mL), cooled at −78° C. was added dropwise 1.4 M n-BuLi (3 mL), followed by 0.5 g of ethyl trifluoroacetate. After stirring for 30 min. at −78° C., 50 mL of Sat. NH$_4$Cl was added and the mixture was extracted with 100 mL of EtOAc. The extract was dried over Na$_2$SO$_4$, concentrated. The residue was purified by flash chromatography eluted with 3:1 Hexane/EtOAc to give 400 mg of the title compound.

Step 5: 3-(4-Phenyl-1-{4-[3-(4-trifluoroacetylphenoxy)propoxy] phenyl}butylthio)propionic acid methyl ester To a stirring solution of the product of Step 4 (270 mg) and methyl 3-mercaptopropionate (250 mL) in 20 mL of CH$_2$Cl$_2$ was added ZnI$_2$ (700 mg) at 0° C. The mixture was stirred for 20 min. at r.t. and then quenched with 20 mL of 25% NH$_4$OAc, extracted with 100 mL of 2:1 Hexane/EtOAc. The organic extract was dried over Na$_2$SO$_4$ and concentrated. The residue was purified by flash chromatography eluted with 5:1 Hexane/EtOAc to give 320 mg of the title compound.

Step 6: 3-(4-Phenyl-1-{4-[3-(4-trifluoroacetylphenoxy) propoxylphenyl}butylthio)propionic acid A mixture of 300 mg of the product from Step 5 and 1.5 mL of 1M LiOH in 12 mL of 5:1 THF/MeOH was stirred for 12 hrs. at r.t. The reaction mixture was then treated with 10 mL of PH-7 buffer and extracted with EtOAc (50 mL). The extract was dried over Na$_2$SO$_4$ and concentrated. The residue was purified by flash chromatography eluted with 2:1 Hexane/EtOAc containing 1% AcOH to give 240 mg of the title compound.

$^1$H NMR (CDCl$_3$ ) δ1.60 (2H, m), 2.86 (2H, m), 2.32 (2H, m), 2.40– 2.60 (6H, m), 3.76 (1H, dd), 4.15 (2H, t), 4.38 (2H, t), 6.84 (2H, d), 7.02 (2H, d), 7.08–7.30 (7H, m), 8.05 (2H, d).

EXAMPLE 8

3-(1-{4-[3-(2-Fluoro-4-trifluoroacetylphenoxy)propoxy] phenyl}- 4-phenylbutylthio)propionic acid Following the procedure described in Step 1–6 of Example 7, but substituting 4-bromophenol for 4-bromo-2-fluorophenol, the title compound was prepared.

$^1$H NMR (CDCl$_3$ ) δ1.58 (2H, m), 1.82 (2H, m), 2.30–2.60 (8H, m), 3.75 (1H, dd), 4.16 (2H, t), 4.35 (2H, t), 6.84 (2H, d), 7.05–7.28 (8H, m), 7.79 (1H, d), 7.65 (1H, d).

EXAMPLE 9

1-(4-Phenyl-1-{4-[3-(4-trifluoroacetylphenoxy)propoxy] phenyl} butylthiomethyl)cyclopropylacetic acid Step 1: 1-(4-Phenyl-1-{4-[3-(4-trifluoroacetylphenoxy)propoxy] phenyl}butylthiomethyl)cyclopropylacetic acid methyl ester Following the procedure in Step 5 of Example 7, but substituting methyl 3-mercaptopropionate for methyl 1-(mercaptomethyl)cyclopropyl acetate (U.S. Pat. No. 5,270,324), the title compound was prepared.

$^1$H NMR (CDCl$_3$ ) δ0.3–0.5 (4H, m), 1.5–1.68 (3H, m), 1.7–1.95 (3H, m), 2.25–2.4 (5H, m), 2.5–2.55 (2H, m), 3.55 (3H, s), 3.75 (1H, dt), 4.13 (2H, t), 4.25 (2H, t), 6.8 (2H, d0, 7.0 (2H, d), 7.08–7.3 (7H, m), 8.02 (2H, d).

Step 2: 1-(4-Phenyl-1-{4-[3-(4-trifluoroacetylphenoxy)propoxy] phenyl}butylthiomethyl)cyclopropylacetic acid Using the procedure described in Step 6 of Example 7, the methyl ester of Step 1 was convened to the title compound.

$^1$H NMR (CDCl$_3$ ) δ0.37–0.48 (4H, m) −7.19 (SH, m), 7.15 (2H, d), 7.05 (2H, d), 6.8 (2H, d), 0.37–0.48 (4H, m), 1.5–1.68 (3H, m), 1.7– 1.9 (3H, m), 2.3 (2H, t), 2.41–2.43 (3H, m), 2.5–2.55 (2H, m), 3.72 (1H, t), 4.13 (2H, t), 4.28 (2H, t), 6.8 (2H, d), 7.05 (2H, d), 7.15 (2H, d), 7.25–7.19 (SH, m), 8.04 (2H, d).

EXAMPLE 10

3-(1-{4-[3-(4-Trifluoroacetylphenoxy)propoxy] phenyl}hexylthio) propionic acid

Step 1: 4-(1-Hydroxyhexyl)phenol

Following the procedure of Step 1 of Example 1, but substituting 3-phenylpropylmagnesium bromide for pentylmagnesium bromide, the title compound was prepared.

Step 2: 1.-{4-[3-(4-Bromophenoxy)propoxy] phenyl}hexan-1-ol

Following the procedure of Step 2 Example 1, but substituting 3-(4-acetyl-3-hydroxy-2-propylphenoxy)propyl bromide for 3-(4-bromophenoxy)propyl bromide (from Step 2, Example 7) and substituting 4-(1-hydroxy-4-phenylbutyl)phenol for the phenol of Step 1, the title compound was prepared.

Step 3: 3-(1-{4-[3-(4-Trifluoroacetylphenoxy)propoxy] phenyl} hexylthio)propionic acid Following the procedure of Steps 4–6 of Example 7, but substituting 1-{4-[3-(4-bromophenoxy)propoxy]phenyl}-4-phenylbutan- 1-ol for the alcohol of Step 2, the title compound was prepared.

$^1$HNMR (CDCl$_3$) δ0.85 (3H, t), 1.25 (6H, m), 1.73–1.89 (2H, m), 2.25–2.38 (2H, m), 2.42–2.6 (4H, m), 3.75 (1H, m), 4.14 (2H, d), 4.32 (2H, d), 6.85 (2H, d), 7.05 (2H, d), 7.23 (2H, d), 8.05 (2H, d).

EXAMPLE 11

3-(1-{4-[3-(3-Methoxy-4-trifluoroacetylphenoxy)propoxy]phenyl}- 4-phenylbutylthio)propiopionic acid.

Following the procedure described in Steps 1–6 of Example 7, but substituting 4-bromophenol for 4-bromo-3-methoxyphenol, the title compound was prepared.

$^1$H NMR (CDCl$_3$ )δ1.5–1.68 (2H, m), 1.80–1.85 (2H, m), 2.28– 2.51 (2H, t), 2.4–2.57 (6H, m), 3.74 (1H, t), 3.86 (3H, s), 4.12 (2H, t), 4.23 (2H, t), 6.47 (1H, s), 6.56 (1H, d), 6.82 (2H, d), 7.09 (2H, d), 7.13– 7.19 (6H, m), 7.72 (1H, d).

EXAMPLE 12

3-(1-{4-[3-(3-Hydroxy-4-trifluoroacetylphenoxy)propoxy]phenyl}- 4-phenylbutylthio)propionic acid Step 1: 4-Bromo-3-methoxymethoxyphenol To a solution of 4-bromoresorcinol (1.5 g) in DMF (15 mL) at 0° C. was added NaH (0.19 g). After 20 min., chloromethylmethyl ether (0.636 g) was added in and stirred for 2 hrs. Saturated aq. NAHCO$_3$ was added and the product was extracted in EtOAc, dried over Na$_2$SO$_4$, and purified by flash chromatography on silica gel with EtOAc in hexanes (1:6).

$^1$H NMR (CDCl$_3$ ) δ3.52 (3H, s), 5.2 (2H, s), 6.38 (1H, dd), 6.68 (1H, d), 7.32 (1H, d).

Step 2: 2,2,2-Trifluoro-1-(4-{3-[3-(1-hydroxy-4-phenylbutyl) phenoxylpropoxy}-2-methoxymethoxyphenyl)ethanone Following the procedure of Steps 1–4 of Example 7, but substituting 4-bromophenol for the phenol from Step 1 the title compound was prepared.

Step 3: 3-(1-{4-[3-(3-Hydroxy-4-trifluoroacetylphenoxy)propoxy] phenyl}-4-phenylbutylthio)propionic acid Using the procedure described in Step 3 of Example 1, the compound of Step 2, was converted to the title compound.

$^1$H NMR δ1.53–1.71 (2H, m), 1.74–1.92 (2H, m), 2.2–2.34 (2H, t), 2.42–2.61 (6H, m), 3.76 (1H, t), 4.12 (2H, t), 4.26 (2H, t), 6.5 (2H, d), 6.8 (2H, d), 7.12 (2H, d), 7.13–7.28 (6H, m), 7.71 (1H, d).

EXAMPLE 13

3-[4-Phenyl-1-(4-{3-[4-(2,2,2-trifluoro-1-hydroxyethyl)phenoxy] propoxy}phenyl)butylthio]propionic acid Step 1: 3-[4-Phenyl-1-(4-{3-[4-(2,2,2-trifluoro-1-hydroxyethyl)phenoxy] propoxy}phenyl)butylthio]propionic acid methyl ester The product from Step 5 of Example 7 (150 mg) was dissolved in 20 mL of MeOH, and treated with 15 mg of NaBH$_4$ at 0° C. After 10 min. the mixture was quenched with 10 mL of sat. NH$_4$Cl, and extracted with 50 mL of EtOAc. The extract was dried over NaSO$_4$ and concentrated to give 150 mg of the title compound.

Step 2: 3-[4-Phenyl-1-(4-{3-[4-(2,2,2-trifluoro-1-hydroxyethyl) phenoxy]propoxy}phenyl)butylthio]propionic acid Using the procedure described in Step 6 of Example 7, the methyl ester (150 mg) was converted to the title compound (94 mg).

$^1$H NMR (CDCl$_3$, 300 MHz) δ1.62 (2H, m), 1.88 (2H, m), 2.24 (2H, q), 2.40–2.65 (6H, m), 3.74 (1H, dd), 4.13 (2H,. t), 4.16 (2H, t), 4.92 (1H, q), 6.83 (2H, d), 6.92 (2H, d), 7.05–7.25 (7H, m), 7.36 (2H, d).

EXAMPLE 14

3-[4-Phenyl-1-(4-{3-[4-(4,4,4-trifluoro-3-oxobutyl)phenoxy]propoxy} phenyl)butylthio]propionic acid Step 1: 3-(4-{3-[4-(1-Hydroxy-4-phenylbutyl)phenoxy] propoxy} phenyl)propionic acid methyl ester Following the procedure of Steps 1–4 of Example 7, but substituting 4-bromophenol for methyl 3-(4-hydroxyphenyl-)propionate, the title compound was prepared.

$^1$H NMR (CD$_3$COCD$_3$) δ1.37–1.92 (10H, m), 2.2 (2H, t), 2.58 (4H, d), 2.85 (2H, t), 3.2–3.31 (1H, m), 3.42–3.58 (2H, m), 3.65 (3H, s), 3.83– 3.94 (1H, m), 4.12 (4H, s), 4.35 (1H, s), 4.5 (1H, t), 4.62 (1H, t), 4.75 (1H, s), 6.82 (4H, m), 7.05–7.3 (9H, m).

Step 2: 3-(4-{3-[4-(1-Hydroxy-4-phenylbutyl)phenoxy] propoxy} phenyl)propionic acid Using the procedure described in Step 6 of Example 7, the methyl ester of Step 1 was converted to the title compound.

Step 3: 3-[4-(3-{4-[1-(2-Methoxycarbonylethylthio)-4-phenylbutyl] phenoxy}propoxy)phenyl]propionic acid Using the method described in Step 5, of Example 7, but substituting 2,2,2-trifluoro-1-(4-{3-[4-(1-hydroxy-4-phenylbutyl) phenoxy]propoxy}phenyl)ethanone for the acid of Step 2, the title compound was obtained.

$^1$H NMR (CD$_3$COCD$_3$) δ1.5–1.68 (2H, m), 1.74–1.92 (2H, m), 2.21 (2H, t), 2.38–2.61 (SH, m), 2.88 (2H, t), 3.62 (3H, s), 3.74 (1H, t), 4.12 (4H, t), 6.82 (4H, d), 7.05–7.28 (9H, m).

Step 4: 3-[4-Phenyl-1-(4-{3-[4-(4,4,4-trifluoro-3-oxobutyl) phenoxy]propoxy}phenyl)butylthio]propionic acid methyl ester Using the method described in literature (*Tetrahedron Lett*, 1992, 33, 1285) the acid of Step 3 (0.237 g) was treated with oxalyl chloride (0.153 mL) and one drop of DMF. After 20 minutes, the solution was evaporated and the residue suspended in dichloromethane. Then the solution was treated with trifluoroacetic anhydride (0.366 mL) and pyridine (0.305 mL). After 3 hrs. the compound was quenched with ice, the compound was purified by flash chromatography on silica with EtOAc and hexanes (1:9).

$^1$H NMR (CD$_3$COCD$_3$) δ1.46–1.68 (2H, m), 1.72–1.91 (2H, m), 2.2 (2H, t), 2.4–2.55 (6H, m), 2.86–3.05 (4H, m), 3.61 (3H, s), 3.75 (1H, t), 4.12 (4H, t), 6.82 (4H, dd), 7.03–7.28 (9H, m).

Step 5: 3-[4-Phenyl-1-(4-{3-[4-(4,4,4-trifluoro-3-oxobutyl)phenoxy] propoxy}phenyl)butylthio]propionic acid Using the procedure as described in Step 6, Example 7, the methyl ester of Step 4 was converted to the title compound.

$^1$H NMR (CD$_3$COCD$_3$) δ1.46–1.68 (2H, m), 1.72–1.91 (2H, m), 2.21 (2H, t), 2.4–2.55 (6H, m), 2.86–3.05 (4H, m), 3.61 (3H, s), 3.75 (1H, t), 4.12 (4H, t), 6.82 (4H, dd), 7.03–7.29 (9H, m).

EXAMPLE 15

3-[ 1-(4-{3-[4-(2,2,3,3,3-Pentafluoropropionyl)phenoxy] propoxy} phenyl)-4-phenylbutylthio]propionic acid Following the procedure described in Steps 4–6 of Example 7, but substituting ethyl trifluoroacetate for ethyl pentafluoroacetate, the title compound was prepared.

$^1$H NMR (CDCl$_3$, 300 MHz) δ1.65 (2H, m), 1.85 (2H, m), 2.82 (2H, m), 2.65–2.90 (6H, m), 3.75 (1H, dd), 4.15 (2H, t), 4.27 (2H, t), 6.83 (2H, d), 7.00 (2H, d), 7.09 (2H, d), 7.12–7.28 (5H, m), 8.06 (2H, d).

EXAMPLE 16

3-(1-{4-[3-(4-Methoxycarbonyloxomethylphenoxy)propoxy]phenyl}-4-phenylbutylthio)propionic acid Step 1: 1-{4-[3-(4-Methoxycarbonyloxomethylphenoxy)propoxy] phenyl}-4-phenylbutan-1-ol Following the procedure described in Step 4 of Example 7, but substituting ethyl trifluoroacetate for dimethyl oxalate, the title compound was prepared.

Step 2: 3-(1-{4-[3-(4-Methoxycarbonyloxomethylphenoxy) propoxy]phenyl}-4-phenylbutylthio}propionic acid Following the procedure described in Step 3 of Example 1, but substituting 1-(2-hydroxy-4-{3-[4-(1-hydroxy-4-phenylbutyl) phenoxy]propoxy}-3-propylphenyl)ethanone for the alcohol from Step 1, the title compound was prepared.

$^1$H NMR (CDCl$_3$) δ1.60 (2H, m), 1.85 (2H, m), 2.30 (2H, m), 2.4–2.6 (6H, m), 3.75 (1H, m), 3.95 (3H, s), 4.14 (2H, t), 4.28 (2H, t), 6.75 (2H, d), 6.98 (2H, d), 7.06–7.30 (7H, m), 8.02 (2H, d).

EXAMPLE 17

3-(1-{4-[2-Pentyloxy-3-(4-trifluoroacetylphenoxy)propoxy]phenyl}- 4-phenylbutylthio)propionic acid Step 1: -[4-(Oxiran-2-ylmethoxy)phenyl]-4-phenylbutan-1-ol To a solution of 5 g of 4-(4 phenyl-2-hydroxybutyl)phenol and 4.88 mL of epichlorohydrine in 4 mL of EtOH was added a solution of 1.26 g of potassium hydroxide in 6 mL of EtOH and 0.12 mL of H$_2$O. After refluxing for 20 min., the mixture was cooled to r.t., quenched with 20 mL of sat. NH$_4$Cl and extracted with 150 mL of 2:1 Hexane/EtOAc. The extract was dried over NaSO$_4$ and concentrated. The residue was purified by flash chromatography eluted with 2:1 Hexane/EtOAc to give 5 g of the title compound.

Step 2: 2-{1-[4-(Oxiran-2-ylmethoxy)phenyl]-4-phenylbutoxy} tetrahydropyran

A solution of the product (5 g) of Step 1 in 150 mL of CH$_2$Cl$_2$ was treated with 10 mL of dihydropyran and 20 mg of PPTS. The mixture was stirred for 4 hrs. at r.t. and then quenched with 0.2 mL of Et$_3$N. Evaporation of solvent gave 5.5 g of the crude title compound.

Step 3: 1-(4-Bromophenoxy)-3-{4-[4-phenyl-1-(tetrahydropyran- 2-yloxy)butyl]phenoxy}propan-2-ol A mixture of the crude product (5.5 g) of Step 2, 4-bromophenol (5.2 g) and 2 drops of Triton B in 30 mL of DMF was heated for 8 hrs. in a 160° C. oil bath. The mixture was then cooled to r.t., quenched with 100 mL of 2N NaOH, and extracted with 200 mL of Et$_2$O. The extract was dried over NaSO$_4$ and concentrated. The crude product was purified by flash chromatography eluted with 2.5:1 Hexane/EtOAc to give 5.2 g of the title compound.

Step 4: 2-(1-{4-[3-(4-Bromophenoxy)-2-pentyloxypropoxy] phenyl}-4-phenylbutoxy)tetrahydropyran A mixture of the product (0.57 g) of Step 3, 0.3 mL of 1-iodopentane and 80 mg of NaH in 20 ml of 1:1 THF/DMF was refluxed for 4 hrs. The mixture was then quenched with 5 mL of MeOH, 20 mL of Sat. NH$_4$Cl, and extracted with 50 mL of Et$_2$O. The extract was dried over NaSO$_4$ and concentrated. The residue was purified by flash chromatography eluted with EtOAc and hexanes (7:1) to give 0.6 g of the title compound.

Step 5: 2,2,2-Trifluoro-1-[4-2-pentyloxy-3-{4-[4-phenyl-1-(tetrahydropyran-2-yloxy)butyl]phenoxy}propoxy) phenyl]ethanone To a solution of the product (0.21 g) of Step 4 in 8 ml of Et$_2$O was added 0.5 mL of 1.4 M tBuLi in pentane at −78° C. After 5 min., 0.25 mL of N-methoxy, N-methyl trifluoro acetamide was added and the mixture was warmed to r.t., quenched with 10 mL of sat. NH$_4$Cl, and extracted with 50 mL of EtOAc. The extract was dried over Na$_2$SO$_4$ and concentrated. The residue was purified by flash chromatography eluted with 8:1 Hexane/EtOAc to give 0.15 g of the title compound.

Step 6: 3-(1-{4-[2-Pentyloxy-3-(4-trifluoroacetylphenoxy) propoxy]phenyl}-4-phenylbutylthio)propionic acid methyl ester A solution of the product (0.4 g) of Step 5 and 0.9 mL of methyl-3-thiopropionate in 20 mL CH$_2$Cl$_2$ was cooled to 0° C. and treated with 1.5 g of ZnI$_2$. After 20 min., the mixture was quenched with 20 ml of 25% NH$_4$OAc, and extracted with 100 mL of EtOAc. The extract was dried over Na$_2$SO$_4$ and concentrated. The residue was purified by flash chromatography eluted with EtOAc and hexanes (1:5) to give 0.4 g of the title compound.

Step 7: 3-(1-{4-[2-Pentyloxy-3-(4-trifluoroacetylphenoxy) propoxy]phenyl}-4-phenylbutylthio)propionic acid Using the procedure described in Step 6 of Example 7, the product (0.4 g) of Step 6 was hydrolized to give 0.28 g of the title compound.

$^1$H NMR (CDCl$_3$) δ0.90 (3H, t), 1.45 (4H, m), 1.60 (4H, m), 1.85 (2H, m), 2.50 (4h, m), 2.58 (2H, m), 3.65–3.80 (3H, m), 4.05 (1H, m), 4.14 (2H, d), 4.31 (1H, dd), 4.34 (1H, dd), 6.86 (2H, d), 7.06 (2H, d), 7.08– 7.26 (7H, m), 8.06 (2H, d).

EXAMPLE 18

3-(1-{4-[2-Benzyloxy-3-(4-trifluoroacetylphenoxy)propoxy]phenyl}- 4-phenylbutylthio)propio acid Following the procedure of Steps 4–7 of Example 17, but substituting 1-iodopentane for benzyl bromide, the title compound was prepared.

$^1$H NMR (CDCl$_3$) δ1.50–1.70 (2H, m), 1.72–1.95 (2H, m), 2.40– 2.60 (6H, m), 3.75 (1H, dd), 4.10–4.20 (1H, m), 4.16 (2H, s), 4.20– 4.36 (2H, m), 4.74–4.82 (2H, 2d, AB), 6.85 (2H, d), 7.00 (2H, d), 7.06–7.40 (12H, m), 8.04 (2H, d).

EXAMPLE 19

3-(4-Phenyl-1-{4-[3-(4-trifluoroacetylphenylthio)propoxy]phenyl} butylthio)propionic acid Following the procedure described in Steps 1–6 of Example 7, but substituting 4-bromophenol for 4-bromothiophenol, the title compound was prepared.

$^1$H NMR (CDCl$_3$) δ1.48–1.72 (2H, m), 1.72–1.95 (2H, m), 2.15–2.14 (2H, m), 2.40–2.60 (6H, m), 3.22 (2H, t), 3.76 (1H, dd), 4.06 (2H, t), 6.82 (2H, d), 7.07–7.27 (7H, m), 7.38 (2H, d), 7.94 (2H, d).

EXAMPLE 20

[1-{4-[3-(4-Acetyl-3-hydroxy-2-propylphenoxy)propoxy]phenyl}-4-( 4-chlorophenyl)butoxy]acetic acid Step 1: [1-{4-[3-(4-Acetyl-3-hydroxy-2-propylphenoxy)propoxy] phenyl}-4-(4-chlorophenyl)butoxy]acetic acid methyl ester Following the procedure of Steps 1–3 of Example 1, but substituting 3-phenylpropylmagnesium bromide for 3-(4-chlorophenylpropylmagnesium bromide, and substituting in Step 3, 3-mercaptopropionic acid for methyl hydroxyacetic acid, and $BF_3.OEt_2$ for $ZnCl_2$, the title compound was prepared.

Step 2: [1-{4-[3-(4-Acetyl-3-hydroxy-2-propylphenoxy)propoxy] phenyl}-4-(4-chlorophenyl)butoxy]acetic acid sodium salt Following the procedure of Step 6 of Example 7, the methyl ester of Step 1 was hydrolyzed to the title compound.

Analysis calculated for $C_{32}H_{36}ClO_7Na.H_2O$: C, 63.10; H, 6.29; Cl, 5.82; Na, 3.77

Found: C, 62.88; H, 6.12; Cl, 6.12; Na, 4.32 with the carbon atoms to which they are attached there is formed a saturated or unsaturated carbon ring of 3, 4, 5, 6, 7 or 8 atoms;

$R^5$ is as defined above or is selected from
(a) hydrogen,
(b) —$C_{1-6}$alkyl,
(c) —$C_{1-6}$alkyl-phenyl$C_{1-6}$alkyl,
(d) —OH,
(e) —O—$C_{1-6}$alkyl, or
(f) —O—$C_{1-6}$alkyl-phenyl$C_{1-6}$alkyl;

TABLE I

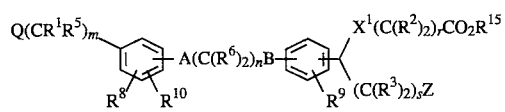

Ia

| EX | $Q(CR^1R^5)_m$ | $R^8$ | $R^{10}$ | A | $R^6$ | $X^1(C(R^2)_2)_rCO_2R^{15}$ | $(C(R^3)_2)_sZ$ |
|----|----|----|----|----|----|----|----|
| 1 | $CH_3CO$ | OH | $(CH_2)_2CH_3$ | O | H | $S(CH_2)_2CO_2H$ | $(CH_2)_3C_6H_5$ |
| 2 | $CH_3CO$ | OH | $(CH_2)_2CH_3$ | O | H | $S(CH_2)_2CO_2Me$ | $(CH_2)_3C_6H_4(4-OH)$ |
| 3 | $CH_3CO$ | OH | $(CH_2)_2CH_3$ | O | H | $SCH_2C(CH_2CH_2)CH_2CO_2H$ | $(CH_2)_3C_6H_5$ |
| 4 | $CH_3CO$ | OH | $(CH_2)_2CH_3$ | O | H | $S(CH_2)_2CO_2H$ | $(CH_2)_2C_6H_5$ |
| 5 | $CH_3CO$ | OH | $(CH_2)_2CH_3$ | O | H | $S(CH_2)_2CO_2Me$ | $(CH_2)_3C_6H_4(4-OH,3I)$ |
| 6 | $CH_3CO$ | OH | H | O | H | $S(CH_2)_2CO_2H$ | $(CH_2)_3C_6H_5$ |
| 7 | $CF_3CO$ | H | H | O | H | $S(CH_2)_2CO_2H$ | $(CH_2)_3C_6H_5$ |
| 8 | $CF_3CO$ | H | F | O | H | $S(CH_2)_2CO_2H$ | $(CH_2)_3C_6H_5$ |
| 9 | $CF_3CO$ | H | H | O | H | $SCH_2C(CH_2CH_2)CH_2CO_2H$ | $(CH_2)_3C_6H_5$ |
| 10 | $CF_3CO$ | H | H | O | H | $S(CH_2)_2CO_2H$ | $(CH_2)_4CH_3$ |
| 11 | $CF_3CO$ | OMe | H | O | H | $S(CH_2)_2CO_2H$ | $(CH_2)_3C_6H_5$ |
| 12 | $CF_3CO$ | OH | H | O | H | $S(CH_2)_2CO_2H$ | $(CH_2)_3C_6H_5$ |
| 13 | $CF_3CH(OH)$ | H | H | O | H | $S(CH_2)_2CO_2H$ | $(CH_2)_3C_6H_5$ |
| 14 | $CF_3C(O)(CH_2)_2$ | H | H | O | H | $S(CH_2)_2CO_2H$ | $(CH_2)_3C_6H_5$ |
| 15 | $C_2F_5C(O)$ | H | H | O | H | $S(CH_2)_2CO_2H$ | $(CH_2)_3C_6H_5$ |
| 16 | $CH_3OC(O)C(O)$ | H | H | O | H | $S(CH_2)_2CO_2H$ | $(CH_2)_3C_6H_5$ |
| 17 | $CF_3CO$ | H | H | O | $O(CH_2)_4CH_3$ | $S(CH_2)_2CO_2H$ | $(CH_2)_3C_6H_5$ |
| 18 | $CF_3CO$ | H | H | O | $OCH_2C_6H_5$ | $S(CH_2)_2CO_2H$ | $(CH_2)_3C_6H_5$ |
| 19 | $CF_3CO$ | H | H | S | H | $S(CH_2)_2CO_2H$ | $(CH_2)_3C_6H_5$ |
| 20 | $CH_3CO$ | OH | $(CH_2)_2CH_3$ | O | H | $OCH_2CO_2H$ | $(CH_2)_3C_6H_4(4-Cl)$ |

What is claimed is:

1. A compound of Formula I

I wherein:
$R^1$ is selected from
(a) hydrogen,
(b) —$C_{1-6}$alkyl, and
(c) —$C_{1-6}$alkyl-phenyl;
or wherein $R^1$ and $R^5$ are joined such that together with the carbon atoms to which they are attached there is formed a saturated or unsaturated carbon ring of 3, 4, 5, 6, 7 or 8 atoms;
$R^2$ and $R^3$ are each independently selected from
(a) hydrogen,
(b) —$C_{1-6}$alkyl,
(c) —$C_{1-6}$alkyl-phenyl,
or wherein two $R^2$ or two $R^3$ are joined such that together $R^6$ is selected from
(a) hydrogen,
(b) —$C_{1-6}$alkyl,
(c) —$C_{1-6}$alkyl-phenyl, wherein the phenyl is optionally substituted with $C_{1-2}$alkyl;
(d) —OH,
(e) —O—$C_{1-6}$alkyl, or
(f) —O—$C_{1-6}$alkyl-phenyl, wherein the phenyl is optionally substituted with $C_{1-2}$alkyl;
or wherein two $R^6$ are joined to form O═ or are joined together such that together with the carbon atom to which they are attached there is formed a saturated or unsaturated carbon ring of 3, 4, 5, 6, 7 or 8 atoms;
$R^8$, $R^9$ and $R^{14}$ are each independently selected from
(a) H,
(b) —$C_{1-6}$alkyl,
(c) halo,
(d) —CN,
(e) —OH,
(f) —$OC_{1-6}$alkyl,
(g) —$OC_{1-6}$alkyl-phenyl, (h) —$SR^{11}$,
(i) $S(O)R^{11}$, or
(j) $S(O)_2R^{11}$;
$R^{10}$, $R^{15}$, $R^{16}$ and $R^{17}$ are each independently selected from
  (a) hydrogen,
  (b) —$C_{1-6}$alkyl, and
  (c) —$C_{1-6}$alkyl-phenyl;
$R^{11}$ is selected from
  (a) —$C_{1-6}$alkyl,
  (b) —$C_{2-6}$alkenyl,
  (c) —$CF_3$,
  (d) —phenyl$(R^{12})_2$, or
  (e) —$C_{2-6}$alkenyl-phenyl$(R^{12})_2$,
$R^{12}$ is
  (a) hydrogen,
  (b) —$C_{1-6}$alkyl,
  (c) Cl, F, I or Br;
$R^{13}$ is perfluoro$C_{1-6}$alkyl;
A and B are each independently
  (a) covalent bond,
  (b) O,
  (c) S,
  (d) S(O), or
  (e) $S(O)_2$;
Q is selected from
  (a) —$CH(OH)R^{13}$,
  (b) —$COR^{13}$,
  (c) —$COR^{16}$, or
  (d) $C_{1-4}$alkyl$COCOOR^{17}$;
$X^1$ is selected from
  (a) —O—,
  (b) —S—,
  (c) —S(O)—,
  (d) —$S(O)_2$—;
Z is
  (a) H, or
  (b) —phenyl—$(R^{14})_3$,
m is 0, 1,2,3 or 4
n is 2,3,4,5,6 or 7;
r and s are each independently 0, 1, 2, 3, 4, 5, 6, 7 or 8.

2. A compound according to claim 1 wherein:
$R^1$ is selected from
  (a) hydrogen, and
  (b) —$C_{1-4}$alkyl;
or wherein $R^1$ and $R^5$ are joined such that together with the carbon atoms to which they are attached there is formed a saturated or unsaturated carbon ring of 3, 4, 5 or 6 atoms;
$R^2$ and $R^3$ are each independently selected from
  (a) hydrogen,
  (b) —$C_{1-5}$alkyl,
or wherein two $R^2$ or two $R^3$ are joined such that together with the carbon atoms to which they are attached there is formed a saturated or unsaturated carbon ring of 3, 4, 5 or 6 atoms;
$R^5$ is as defined above or is selected from
  (a) hydrogen,
  (b) —$C_{1-3}$alkyl,
  (c) —OH,
  (d) —O—$C_{1-3}$alkyl, or
$R^6$ is selected from
  (a) hydrogen,
  (b) —$C_{1-3}$alkyl,
  (c) —OH,
  (d) —O—$C_{1-3}$alkyl, or
$R^8$, $R^9$ and $R^{14}$ are each independently selected from
  (a) H,
  (b) —$C_{1-4}$alkyl,
  (c) F, Cl or Br,
  (d) —OH,
  (e) —$OC_{1-4}$alkyl,
  (f) —$SR^{11}$,
  (g) $S(O)R^{11}$, or
  (h) $S(O)_2R^{11}$;
$R^{10}$, $R^{15}$, $R^{16}$ and $R^{17}$ are each independently selected from
  (a) hydrogen,
  (b) —$C_{1-4}$alkyl, and
  (c) —$C_{1-4}$alkyl-phenyl;
$R^{11}$ is selected from
  (a) —$C_{1-2}$alkyl,
  (b) —$C_{2-6}$alkenyl,
  (c) —$CF_3$,
  (d) —phenyl$(R^{12})_2$, or
  (e) —$C_{2-6}$alkenyl—phenyl$(R^{12})_2$,
$R^{12}$ is
  (a) hydrogen,
  (b) —$C_{1-6}$alkyl,
  (c) Cl, F, I or Br;
$R^{13}$ is perfluoro$C_{1-6}$alkyl;
A and B are each independently
  (a) covalent bond,
  (b) O,
  (c) S,
  (d) S(O), or
  (e) $S(O)_2$;
Q is selected from
  (a) —$CH(OH)R^{13}$,
  (b) —$COR^{13}$,
  (c) —$COR^{16}$, or
  (d) —$C_{1-4}$alkyl$COCOOR^{17}$;
X is selected from
  (a) —O—,
  (b) —S—,
  (c) —S(O)—,
  (d) —$S(O)_2$—;
Z is
  (a) H, or
  (b) —phenyl—$(R^{14})_2$,
m is 0, 1, 2 or 3
n is 2, 3, 4 or 5;
r and s are each independently 0, 1, 2, 3, 4, 5 or 6.

3. A compound according to claim 2 wherein:
$R^1$ is selected from
  (a) hydrogen, and
  (b) —$C_{1-4}$alkyl;
$R^2$ and $R^3$ are each independently selected from
  (a) hydrogen,
  (b) —$C_{1-5}$alkyl, or wherein two $R^2$ or two $R^3$ are joined such that together with the carbon atoms to which they are attached there is formed a saturated or unsaturated carbon ring of 3, 4, 5 or 6 atoms;

$R^5$ is as defined above or is selected from
 (a) hydrogen,
 (b) —$C_{1-3}$alkyl,
 (c) —OH,
 (d) —O—$C_{1-3}$alkyl, or $R^6$ is selected from
 (a) hydrogen,
 (b) —$C_{1-3}$alkyl,
 (c) —OH,
 (d) —O—$C_{1-3}$alkyl, or $R^8$, $R^9$ and $R^{14}$ are each independently selected from
 (a) H,
 (b) —$C_{1-4}$alkyl,
 (c) F, Cl or Br,
 (d) —OH,
 (e) —O$C_{1-4}$alkyl,
 (f) —$SR^{11}$,
 (g) $S(O)R^{11}$, or
 (h) $S(O)_2R^{11}$;

$R^{10}$, $R^{15}$, $R^{16}$ and $R^{17}$ are each independently selected from
 (a) hydrogen,
 (b) —$C_{1-4}$alkyl, and
 (c) —$C_{1-4}$alkyl-phenyl;

$R^{11}$ is selected from
 (a) —$C_{1-2}$alkyl,
 (b) —$CF_3$,
 (c) —phenyl($R^{12}$), or $R^{12}$ is
 (a) hydrogen,
 (b) —$C_{1-3}$alkyl,
 (c) Cl, F, I or Br;

is perfluoro$C_{1-2}$alkyl;

A and B are each independently
 (a) covalent bond,
 (b) O,
 (c) S,
 (d) S(O), or
 (e) $S(O)_2$;

is selected from
 (a) —CH(OH)$R^{13}$,
 (b) —$COR^{13}$,
 (c) —$COR^{16}$, or
 (d) —$C_{1-4}$alkylCOCOO$R^{17}$;

$X^1$ is selected from
 (a) —O—,
 (b) —S—,
 (c) —S(O)—,
 (d) —$S(O)_2$—;

Z is
 (a) H, or
 (b) —phenyl—$(R^{14})_2$, m is 0, 1, 2 or 3
n is 2, 3, 4 or 5;
r and s are each independently 0, 1, 2, 3 or 4.

4. A compound according to claim 3 wherein:

$R^1$ is selected from
 (a) hydrogen, and
 (b) —$C_{1-3}$alkyl;

or wherein $R^1$ and $R^5$ are joined such that together with the carbon atoms to which they are attached there is formed a saturated or unsaturated carbon ring of 3, 4, 5, 6, 7 or 8 atoms;

$R^2$ and $R^3$ are each independently selected from
 (a) hydrogen,
 (b) —$C_{1-5}$alkyl, or wherein two $R^2$ or two $R^3$ are joined such that together with the carbon atoms to which they are attached there is formed a saturated or unsaturated carbon ring of 3, 4, 5 or 6 atoms;

$R^5$ is as defined above or is selected from
 (a) hydrogen,
 (b) —$C_{1-3}$alkyl,
 (c) —OH,
 (d) —O—$C_{1-3}$alkyl, or $R^6$ is selected from
 (a) hydrogen,
 (b) —$C_{1-3}$alkyl,
 (c) —OH,
 (d) —O—$C_{1-3}$alkyl, or $R^8$, $R^9$ and $R^{14}$ are each independently selected from
 (a) H,
 (b) —$C_{1-3}$alkyl,
 (c) F, Cl or Br,
 (d) —OH, or
 (e) —O$C_{1-3}$alkyl;

$R^{10}$, $R^{15}$, $R^{16}$ and $R^{17}$ are each independently selected from
 (a) hydrogen,
 (b) —$C_{1-3}$alkyl, and
 (c) —$C_{1-3}$alkyl-phenyl;

$R^{11}$ is selected from
 (a) —$C_{1-2}$alkyl,
 (b) —$CF_3$, or
 (c) —phenyl($R^{12}$);

$R^{12}$ is
 (a) hydrogen,
 (b) —$C_{1-3}$alkyl,
 (c) Cl, F, I or Br;

$R^{13}$ is perfluoro$C_{1-2}$alkyl;

A and B are each independently
 (a) —O—, or
 (b) —S—,

Q is selected from
 (a) —CH(OH)$R^{13}$,
 (b) —$COR^{13}$,
 (c) —$COR^{16}$, or
 (d) —$C_{1-4}$alkylCOCOO$R^{17}$;

$X^1$ is selected from
 (a) —O—,
 (b) —S—,

Z is
 (a) H, or
 (b) —phenyl—$(R^{14})$, m is 0, 1 or 2
n is 2, 3 or 4;

r and s are each independently 0, 1, 2, 3 or 4.

5. A compound of formula Ia according to claim 1

$$Q(CR^1R^5)_m \text{—Ar—A—CH}(R^6)\text{—CH}_2\text{—O—Ar'—CH}(X^1(C(R^2)_2)_rCO_2R^{15})((C(R^3)_2)_sZ) \quad \text{Ia}$$

(with $R^8$ and $R^{10}$ on the first aryl ring)

wherein:

$R^1$ is selected from
 (a) hydrogen,
 (b) —$C_{1-6}$alkyl, and
 (c) —$C_{1-6}$alkyl-phenyl;
or $R^1$ and $R^5$ are joined such that together with the carbon atoms to which they are attached there is formed a saturated or unsaturated carbon ring of 3, 4, 5, 6, 7 or 8 atoms;

$R^2$ and $R^3$ are each independently selected from
 (a) hydrogen,
 (b) —$C_{1-6}$alkyl,
 (c) —$C_{1-6}$alkyl-phenyl,
or wherein two $R^2$ groups or two $R^3$ groups are joined such that together with the carbon atoms to which they are attached there is formed a saturated or unsaturated carbon ring of 3, 4, 5, 6, 7 or 8 atoms;

$R^5$ is as defined above or is selected from
 (a) hydrogen,
 (b) —$C_{1-6}$alkyl,
 (c) —$C_{1-6}$alkyl-phenyl$C_{1-6}$alkyl,
 (d) —OH,
 (e) —O—$C_{1-6}$alkyl, or
 (f) —O—$C_{1-6}$alkyl-phenyl$C_{1-6}$alkyl;

$R^6$ is selected from
 (a) hydrogen,
 (b) —$C_{1-6}$alkyl,
 (c) —$C_{1-6}$alkyl-phenyl, wherein the phenyl is optionally substituted with $C_{1-2}$alkyl;
 (d) —OH,
 (e) —O—$C_{1-6}$alkyl, or
 (f) —O—$C_{1-6}$alkyl-phenyl$C_{1-6}$alkyl, wherein the phenyl is optionally substituted with $C_{1-2}$alkyl;
or wherein two $R^6$ groups are joined to form O= or are joined together such that together with the carbon atom to which they are attached there is formed a saturated or unsaturated carbon ring of 3, 4, 5, 6, 7 or 8 atoms;

$R^8$ and $R^{14}$ are each independently selected from
 (a) H,
 (b) —OH, or
 (c) —OCH$_3$;

$R^{10}$ is selected from
 (a) hydrogen, and
 (b) —$C_{1-6}$alkyl;

$R^{13}$ is perfluoro$C_{1-6}$alkyl;

$R^{15}$, $R^{16}$ and $R^{17}$ are each independently selected from
 (a) hydrogen,
 (b) —$C_{1-6}$alkyl, and
 (c) —$C_{1-6}$alkyl-phenyl;

A is
 (a) O,
 (b) S,

Q is selected from
 (a) —CH(OH)$R^{13}$,
 (b) —COR$^{13}$,
 (c) —COR$^{16}$,
 (d) —$C_{1-4}$alkyl-COR$^{17}$, or
 (e) —$C_{1-4}$alkylCOCOOR$^{17}$;

$X^1$ is selected from
 (a) —O—,
 (b) —S—,

Z is
 (a) H, or
 (b) —phenyl—(R$^{14}$)$_3$, m is 0, 1, 2, 3 or 4 r and s are each independently 0, 1, 2, 3, 4, 5, 6, 7 or 8.

6. A compound according to claim 5 wherein:

$R^1$ is selected from
 (a) hydrogen,
 (b) —$C_{1-3}$alkyl,
 (c) —OH, and
 (d) —O—$C_{1-3}$alkyl;

$R^2$ is selected from
 (a) hydrogen,
 (b) —$C_{1-3}$alkyl,
 (c) —$C_{1-3}$alkyl-phenyl,
or wherein two $R^2$ groups are joined such that together with the carbon atoms to which they are attached there is formed a saturated or unsaturated carbon ring of 3, 4, 5 or 6 atoms;

$R^3$ is hydrogen, $R^5$ is selected from
 (a) hydrogen,
 (b) —$C_{1-3}$alkyl,
 (c) —OH, and
 (d) —O—$C_{1-3}$alkyl;

$R^6$ is selected from
 (a) hydrogen,
 (b) —$C_{1-3}$alkyl,
 (c) —OH,
 (d) —O—$C_{1-5}$alkyl, or
 (e) —O—$C_{1-3}$alkyl-phenyl, wherein the phenyl is optionally substituted with $C_{1-2}$alkyl;

$R^8$ and $R^{14}$ are each independently selected from
 (a) H,
 (b) —OH, or
 (c) —OCH$_3$;

$R^{10}$ is selected from
 (a) hydrogen, and
 (b) —$C_{1-6}$alkyl;

$R^{13}$ is perfluoro$C_{1-6}$alkyl;

$R^{15}$, $R^{16}$ and $R^{17}$ are each independently selected from (a) hydrogen, (b) —$C_{1-6}$alkyl, and (c) —$C_{1-4}$alkyl-phenyl;

A is (a) O, (b) S,

Q is selected from (a) —CH(OH)$R^{13}$, (b) —CO$R^{13}$, (c) —CO$R^{16}$, (d) —$C_{1-4}$alkyl-CO$R^{17}$, or (e) —$C_{1-4}$alkylCOCOO$R^{17}$;

$X^1$ is selected from (a) —O—, (b) —S—,

Z is (a) H, or (b) —phenyl—$(R^{14})_3$, m is 0, 1, 2 or 3 r and s are each independently 0, 1, 2, 3, 4, 5 or 6.

7. A compound according to claim 6 wherein:

$R^1$ is selected from (a) hydrogen, (b) —$C_{1-3}$alkyl, $R^2$ is selected from (a) hydrogen, (b) —$C_{1-3}$alkyl, (c) —$C_{1-3}$alkyl-phenyl, or wherein two $R^2$ groups are joined such that together with the carbon atoms to which they are attached there is formed a cyclopropyl group;

$R^3$ is hydrogen, $R^5$ is selected from (a) hydrogen, (b) —$C_{1-3}$alkyl, $R^6$ is selected from (a) hydrogen, (b) —$C_{1-3}$alkyl, (d) —O—$C_{1-4}$alkyl, or (e) —O—$C_{1-3}$alkyl-phenyl;

$R^8$ and $R^{14}$ are each independently selected from (a) H, (b) —OH, or (c) —OCH$_3$;

$R^{10}$ is selected from (a) hydrogen, and (b) —$C_{1-4}$alkyl;

$R^{13}$ is perfluoro$C_{1-6}$alkyl;

$R^{15}$, $R^{16}$ and $R^{17}$ are each independently selected from (a) hydrogen, (b) —$C_{1-4}$alkyl, and (c) —$C_{1-4}$alkyl-phenyl;

A is (a) O, (b) S,

Q is selected from (a) —CH(OH)$R^{13}$, (b) —CO$R^{13}$, (c) —CO$R^{16}$, (d) —$C_{1-4}$alkyl-CO$R^{17}$, or (e) —$C_{1-4}$alkylCOCOO$R^{17}$;

$X^1$ is selected from (a) —O—, (b) —S—,

Z is (a) H, or (b) —phenyl—$(R^{14})_2$, m is 0, 1, 2 or 3;

r and s are each independently 0, 1, 2, 3 or 4.

8. A compound according to claim 7 wherein:

$R^1$ is selected from (a) hydrogen, (b) —$C_{1-2}$alkyl, $R^2$ is selected from (a) hydrogen, (b) —$C_{1-2}$alkyl, (c) —$C_{1-2}$alkyl-phenyl, or wherein two $R^2$ groups are joined such that together with the carbon atoms to which they are attached there is formed a cyclopropyl group;

$R^3$ is hydrogen, $R^5$ is selected from is (a) hydrogen, (b) —$C_{1-2}$alkyl, $R^6$ is selected from (a) hydrogen, (b) —$C_{1-2}$alkyl, (d) —O—$C_{1-3}$alkyl, or (e) —O—$C_{1-2}$alkyl-phenyl;

$R^8$ and $R^{14}$ are each independently selected from (a) H, (b) —OH, or (c) —OCH$_3$;

$R^{10}$ is selected from (a) hydrogen, and (b) —$C_{1-3}$alkyl;

$R^{13}$ is perfluoro$C_{1-6}$alkyl;

$R^{15}$, $R^{16}$ and $R^{17}$ are each independently selected from (a) hydrogen, (b) —$C_{1-3}$alkyl, and (c) —$C_{1-3}$alkyl-phenyl;

A is (a) O, (b) S,

Q is selected from (a) —CH(OH)$R^{13}$, (b) —CO$R^{13}$, (c) —CO$R^{16}$, (d) —$C_{1-4}$alkyl-CO$R^{17}$, or (e) —$C_{1-4}$alkylCOCOO$R^{17}$;

$X^1$ is selected from (a) —O—, (b) —S—,

Z is (a) H, or (b) —phenyl—$(R^{14})$, m is 0, 1 or 2;

r and s are each independently 0, 1, 2 or 3.

9. A compound of formula Ia according to claim 8 wherein:

Q is
- (a) —C(O)—CH$_3$,
- (b) —C(O)—CF$_3$,
- (c) —CH$_2$CH$_2$—C(O)—CF$_3$
- (d) —CH(OH)—CF$_3$,
- (e) —C(O)—C$_2$F$_5$, or
- (f) —C(O)—C(O)—O—CH$_3$;

R$^2$ is
- (a) hydrogen,
- (b) methyl, or
- (c) ethyl;

R$^3$ is hydrogen;

R$^6$ is
- (a) hydrogen,
- (b) —O—CH$_2$—C$_6$H$_5$, or
- (c) —O—(CH$_2$)$_4$—CH$_3$;

R$^8$ is
- (a) hydrogen,
- (b) —OH, or
- (c) —OMe;

R$^{10}$ is
- (a) hydrogen, or
- (b) n-propyl;

R$^{14}$ is hydroxy, I or Cl;

R$^{15}$ is
- (a) hydrogen, or
- (b) methyl;

A is
- (a) O,
- (b) S;

X$^1$ is
- (a) —S—, or
- (b) —O;

Z is
- (a) H, or
- (b) —phenyl—(R$^{14}$);

m is 0 or 1;

r is 1 or 2;

10. A compound according to claim 9 selected from the group consisting of (a) 3-(1-{4-[3-(4-Acetyl-3-hydroxy-2-propylphenoxy) propoxy]phenyl}-4-phenylbutylthio)propionic acid sodium salt, (b) 3-[1-{4-[3-(4-Acetyl-3-hydroxy-2-propylphenoxy) propoxy]phenyl}-4-(4-hydroxyphenyl)butylthio]propionic acid methyl ester, (c) 1-(1-{4-[3-(4-Acetyl-3-hydroxy-2-propylphenoxy) propoxy]phenyl}-4-phenylbutylthiomethyl) cyclopropylacetic acid, (d) 3-(1-{4-[3-(4-Acetyl-3-hydroxy-2-propylphenoxy) propoxy]phenyl}-3-phenylpropylthio)propionic acid, (e) 3-[ 1-{4-[3-(4-Acetyl-3-hydroxy-2-propylphenoxy) propoxy]phenyl}-4-(4-hydroxy-3-iodophenyl) butylthio]propionic acid methyl ester, (f) 3-(1-{4-[3-(4-Acetyl-3-hydroxyphenoxy)propoxy] phenyl}-4-phenylbutylthio)propionic acid sodium salt, (g) 3-(4-Phenyl-1-{4-[3-(4-trifluoroacetylphenoxy) propoxy]phenyl} butylthio)propionic acid, (h) 3-(1-{4-[3-(2-Fluoro-4-trifluoroacetylphenoxy) propoxy]phenyl}-4-phenylbutylthio)propionic acid, (i) 1-(4-Phenyl-1-{4-[3-(4-trifluoroacetylphenoxy) propoxy]phenyl}butylthiomethyl)cyclopropyl acetic acid, (j) 3-(1-{4-[3-(4-Trifluoroacetylphenoxy)propoxy]phenyl} hexylthio)propionic acid, (k) 3-(1-{4-[3-(3-Methoxy-4-trifluoroacetylphenoxy) propoxy]phenyl}-4-phenylbutylthio)propionic acid, (l) 3-(1-{4-[3-(3-Hydroxy-4-trifluoroacetylphenoxy) propoxy]phenyl}-4-phenylbutylthio)propionic acid, (m) 3-[4-Phenyl-1-(4-{3-[4-(2,2,2-trifluoro-1-hydroxyethyl) phenoxy]propoxy}phenyl)butylthio]propionic acid, (n) 3-[4-Phenyl-1-(4-{3-[4-(4,4,4-trifluoro-3-oxobutyl) phenoxy]propoxy}phenyl)butylthio]propionic acid, (o) 3-[ 1-(4-{3-[4-(2,2,3,3,3-Pentafluoropropionyl)phenoxy] propoxy}phenyl)-4-phenylbutylthio]propionic acid, (p) 3-(1-{4-[3-(4-Methoxycarbonyloxomethylphenoxy) propoxy)phenyl}-4-phenylbutylthio)propionic acid, (q) 3-(1-{4-[2-Pentyloxy-3-(4-trifluoroacetylphenoxy) propoxy]phenyl}-4-phenylbutylthio)propionic acid, (r) 3-(1-{4-[2-Benzyloxy-3-(4-trifluoroacetylphenoxy) propoxy]phenyl}-4-phenylbutylthio)propionic acid, (s) 3-(4-Phenyl-1-{4-[3-(4-trifluoroacetylphenylthio) propoxy]phenyl}butylthio)propionic acid, and (t) [ 1-{4-[3-(4-Acetyl-3-hydroxy-2-propylphenoxy) propoxy]phenyl}-4-(4-chlorophenyl)butoxy]acetic acid 11. A pharmceutical composition for the inhibition of phospholipase A$_2$ comprising a pharmaceutically acceptable carder and a non-toxic, therapeutically effective amount of a compound according to claim 1.

12. A method of inhibiting phospholipase A$_2$ in an a patient in need thereof comprising: administration to a patient in need of said inhibition of a non-toxic therapeuticaly effective amount of a compound according to claim 1.

* * * * *